United States Patent [19]

Khandke

[11] Patent Number: 5,578,480
[45] Date of Patent: Nov. 26, 1996

[54] METHODS FOR THE ISOLATION AND PURIFICATION OF THE RECOMBINANTLY EXPRESSED CHONDROITINASE I AND II ENZYMES FROM *P. VULGARIS*

[75] Inventor: Kiran M. Khandke, Nanuet, N.Y.

[73] Assignee: American Cyanamid Company, Wayne, N.J.

[21] Appl. No.: 233,008

[22] Filed: Apr. 22, 1994

Related U.S. Application Data

[63] Continuation-in-part of Ser. No. 52,206, Apr. 23, 1993, abandoned.
[51] Int. Cl.⁶ .............................. C12N 9/88; C12N 15/60
[52] U.S. Cl. ..................... 435/232; 435/69.1; 530/417
[58] Field of Search ................................. 435/232

[56] References Cited

U.S. PATENT DOCUMENTS 5,198,355 2/1993 Kikuchi et al. ....................... 435/232

OTHER PUBLICATIONS

Scopes (1982) Protein Purification. New York: Springer Verlag. pp. 197–199.
Yamagata et al. (1968) J. Biol. Chem 243: 1523–1535.

*Primary Examiner*—Robert A. Wax
*Assistant Examiner*—Gabriele E. Bugaisky
*Attorney, Agent, or Firm*—Darby & Darby, P.C.

[57] ABSTRACT

This invention relates to methods for the isolation and purification of the recombinantly expressed major protein component of chondroitinase ABC, which is referred to as "chondroitinase I", from *Proteus vulgaris* (*P. vulgaris*). This invention further relates to methods for the isolation and purification of the recombinantly expressed second protein component of chondroitinase ABC, which is referred to as "chondroitinase II", from *P. vulgaris*. These methods provide significantly higher yields and purity than those obtained by adapting for the recombinant enzymes the method previously used for isolating and purifying native chondroitinase I enzyme from *P. vulgaris*.

24 Claims, 3 Drawing Sheets

METHODS FOR THE ISOLATION AND PURIFICATION OF THE RECOMBINANTLY EXPRESSED CHONDROITINASE I AND II ENZYMES FROM P. VULGARIS

This application is a continuation-in-part of U.S. Ser. No. 08/052,206, filed Apr. 23, 1993, now abandoned which is incorporated herein by reference in its entirety.

FIELD OF THE INVENTION

This invention relates to methods for the isolation and purification of the recombinantly expressed major protein component of chondroitinase ABC, which is referred to as "chondroitinase I", from *Proteus Vulgaris* (*P. vulgaris*). This invention further relates to methods for the isolation and purification of the recombinantly expressed second protein component of chondroitinase ABC, which is referred to as "chondroitinase II", from *P. vulgaris*. These methods provide significantly higher yields and purity than those obtained by adapting for the recombinant enzymes the method previously used for isolating and purifying the native chondroitinase I enzyme from *P. vulgaris*.

BACKGROUND OF THE INVENTION

Chondroitinases are enzymes of bacterial origin which have been described as having value in dissolving the cartilage of herniated discs without disturbing the stabilizing collagen components of those discs.

Examples of chondroitinase enzymes are chondroitinase ABC, which is produced by the bacterium *P. vulgaris*, and chondroitinase AC, which is produced by *A. aurescens*. The chondroitinases function by degrading polysaccharide side chains in protein-polysaccharide complexes, without degrading the protein core.

Yamagata et al. describes the purification of the enzyme chondroitinase ABC from extracts of *P. vulgaris* (Bibliography entry 1). The enzyme selectively degrades the glycosaminoglycans chondroitin-4-sulfate, dermatan sulfate and chondroitin-6-sulfate (also referred to respectively as chondroitin sulfates A, B and C) at pH 8 at higher rates than chondroitin or hyaluronic acid. However, the enzyme did not attack keratosulfate, heparin or heparitin sulfate.

Kikuchi et al. describes the purification of glycosaminoglycan degrading enzymes, such as chondroitinase ABC, by fractionating the enzymes by adsorbing a solution containing the enzymes onto an insoluble sulfated polysaccharide carrier and then desorbing the individual enzymes from the carrier (2).

Brown describes a method for treating intervertebral disc displacement in mammals, including humans, by injecting into the intervertebral disc space effective amounts of a solution containing chondroitinase ABC (3). The chondroitinase ABC was isolated and purified from extracts of *P. vulgaris*. This native enzyme material functioned to dissolve cartilage, such as herniated spinal discs. Specifically, the enzyme causes the selective chemonucleolysis of the nucleus pulposus which contains proteoglycans and randomly dispersed collagen fibers.

Hageman describes an ophthalmic vitrectomy method for selectively and completely disinserting the ocular vitreous body, epiretinal membranes or fibrocellular membranes from the neural retina, ciliary epithelium and posterior lens surface of the mammalian eye as an adjunct to vitrectomy, by administering to the eye an effective amount of an enzyme which disrupts or degrades chondroitin sulfate proteoglycan localized specifically to sites of vitreoretinal adhesion and thereby permit complete disinsertion of said vitreous body and/or epiretinal membranes (4). The enzyme can be a protease-free glycosaminoglycanase, such as chondroitinase ABC. Hageman utilized chondroitinase ABC obtained from Seikagaku Kogyo Co., Ltd., Tokyo, Japan.

In isolating and purifying the chondroitinase ABC enzyme from the Seikagaku Kogyo material, it was noted that there was a correlation between effective preparations of the chondroitinase in vitrectomy procedures and the presence of a second protein having an apparent molecular weight (by SDS-PAGE) slightly greater than that of the major protein component of chondroitinase ABC. The second protein is now designated the "chondroitinase II", while the major protein component of chondroitinase ABC is referred to as the "chondroitinase I." The chondroitinase I and II proteins are basic proteins at neutral pH, with similar isoelectric points of 8.30–8.45. Separate purification of the chondroitinase I and II forms of the native enzyme revealed that it was the combination of the two proteins that was active in the surgical vitrectomy rather than either of the proteins individually.

Use of the chondroitinase I and II forms of the native enzyme to date has been limited by the small amounts of enzymes obtained from native sources. The production and purification of the native forms of the enzyme has been carried out using fermentations of *P. vulgaris* in which its substrate has been used as the inducer to initiate production of these forms of the enzyme. A combination of factors, including low levels of synthesis, the cost and availability of the inducer (chondroitin sulfate), and the opportunistically pathogenic nature of *P. vulgaris*, has resulted in the requirement for a more efficient method of production. In addition, the native forms of the enzyme produced by conventional techniques are subject to degradation by proteases present in the bacterial extract. Therefore, there is a need for methods to isolate and purify a reliable supply of the chondroitinase I and II enzymes free of contaminants in order for the medical applications of the two forms of this enzyme to be evaluated properly and exploited.

SUMMARY OF THE INVENTION

Accordingly, it is an object of this invention to provide methods for the isolation and purification of the recombinantly expressed chondroitinase I enzyme of *P. vulgaris*.

It is a particular object of this invention to provide methods which result in significantly higher yields and purity of the recombinant chondroitinase I enzyme than those obtained by adapting for the recombinant enzyme the method previously used for isolating and purifying the native chondroitinase I enzyme from *P. vulgaris*.

These objects are achieved through either of two methods described and claimed herein for the chondroitinase I enzyme. The first method comprises the steps of:

(a) lysing by homogenization the host cells which express the recombinant chondroitinase I enzyme to release the enzyme into the supernatant;

(b) subjecting the supernatant to diafiltration to remove salts and other small molecules;

(c) passing the supernatant through an anion exchange resin-containing column;

(d) loading the eluate from step (c) to a cation exchange resin-containing column so that the enzyme in the eluate binds to the cation exchange column; and (e) eluting the enzyme bound to the cation exchange column with a solvent capable of releasing the enzyme from the column.

In the second method, prior to step (b) of the first method just described, the following two steps are performed:

(1) treating the supernatant with an acidic solution to precipitate out the enzyme; and (2) recovering the pellet and then dissolving it in an alkali solution to again place the enzyme in a basic environment.

It is a further object of this invention to provide methods for the isolation and purification of the recombinantly expressed chondroitinase II enzyme of *P. vulgaris*.

It is an additional object of this invention to provide methods which result in significantly higher yields and purity of the recombinant chondroitinase II enzyme than those obtained by adapting for the recombinant enzyme the method previously used for isolating and purifying the native chondroitinase I enzyme from *P. vulgaris*.

These objects are achieved through either of two methods described and claimed herein for the chondroitinase II enzyme. The first method comprises the steps of:

(a) lysing by homogenization the host cells which express the recombinant chondroitinase I enzyme to release the enzyme into the supernatant;

(b) subjecting the supernatant to diafiltration to remove salts and other small molecules;

(c) passing the supernatant through an anion exchange resin-containing column;

(d) loading the eluate from step (c) to a cation exchange resin-containing column so that the enzyme in the eluate binds to the cation exchange column;

(e) obtaining by affinity elution the enzyme bound to the cation exchange column with a solution of chondroitin sulfate, such that the enzyme is co-eluted with the chondroitin sulfate;

(f) loading the eluate from step (e) to an anion exchange resin-containing column and eluting the enzyme with a solvent such that the chondroitin sulfate binds to the column; and (g) concentrating the eluate from step (f) and crystallizing out the enzyme from the supernatant which contains an approximately 37 kD contaminant.

In the second method, prior to step (b) of the first method just described, the following two steps are performed:

(1) treating the supernatant with an acidic solution to precipitate out the enzyme; and (2) recovering the pellet and then dissolving it in an alkali solution to again place the enzyme in a basic environment.

Use of the methods of this invention results in significantly higher yields and purity of each recombinant enzyme than those obtained by adapting for each recombinant enzyme the method previously used for isolating and purifying the native chondroitinase I enzyme from *P. vulgaris*.

DETAILED DESCRIPTION OF THE INVENTION

Initial attempts to isolate and purify the recombinant chondroitinase I enzyme do not result in high yields of purified protein. The previous method for isolating and purifying native chondroitinase I from fermentation cultures of *P. vulgaris* is found to be inappropriate for the recombinant material.

The native enzyme is produced by fermentation of a culture of *P. vulgaris*. The bacterial cells are first recovered from the medium and resuspended in buffer. The cell suspension is then homogenized to lyse the bacterial cells. Then a charged particulate such as Bioacryl (Toso Haas, Philadelphia, Pa.), is added to remove DNA, aggregates and debris from the homogenization step. Next, the solution is brought to 40% saturation of ammonium sulfate to precipitate out undesired proteins. The chondroitinase I remains in solution.

The solution is then filtered and the retentate is washed to recover most of the enzyme. The filtrate is concentrated and subjected to diafiltration with a phosphate to remove the salt.

The filtrate containing the chondroitinase I is subjected to cation exchange chromatography using a cellulose sulfate column. At pH 7.2, 20 mM sodium phosphate, more than 98% of the chondroitinase I binds to the column. The native chondroitinase I is then eluted from the column using a sodium chloride gradient.

The eluted enzyme is then subjected to additional chromatography steps, such as anion exchange and hydrophobic interaction column chromatography. As a result of all of these procedures, chondroitinase I is obtained at a purity of 90–97%. The level of purity is measured by first performing SDS-PAGE. The proteins are stained using Coomassie blue, destained, and the lane on the gel is scanned using a laser beam of wavelength 600 nm. The purity is expressed as the percentage of the total absorbance accounted for by that band.

However, the yield of the native protein is only 25–35%. The yield is measured as the remaining activity in the final purified product, expressed as a percentage of the activity at the start (which is taken as 100%). In turn, the activity of the enzyme is based on measuring the release of unsaturated disaccharide from chondroitin sulfate C at 232 nm.

This purification method also results in the extensive cleavage of the approximately 110,000 dalton (110 kD) chondroitinase I protein into a 90 kD and an 18 kD fragment. Nonetheless, the two fragments remain non-covalently bound and exhibit chondroitinase I activity.

When this procedure is repeated with homogenate from lysed host cells carrying a recombinant plasmid encoding chondroitinase I, significantly poorer results are obtained. Less than 10% of the chondroitinase I binds to the cation exchange column at standard stringent conditions of pH 7.2, 20 mM sodium phosphate.

Figure 1:
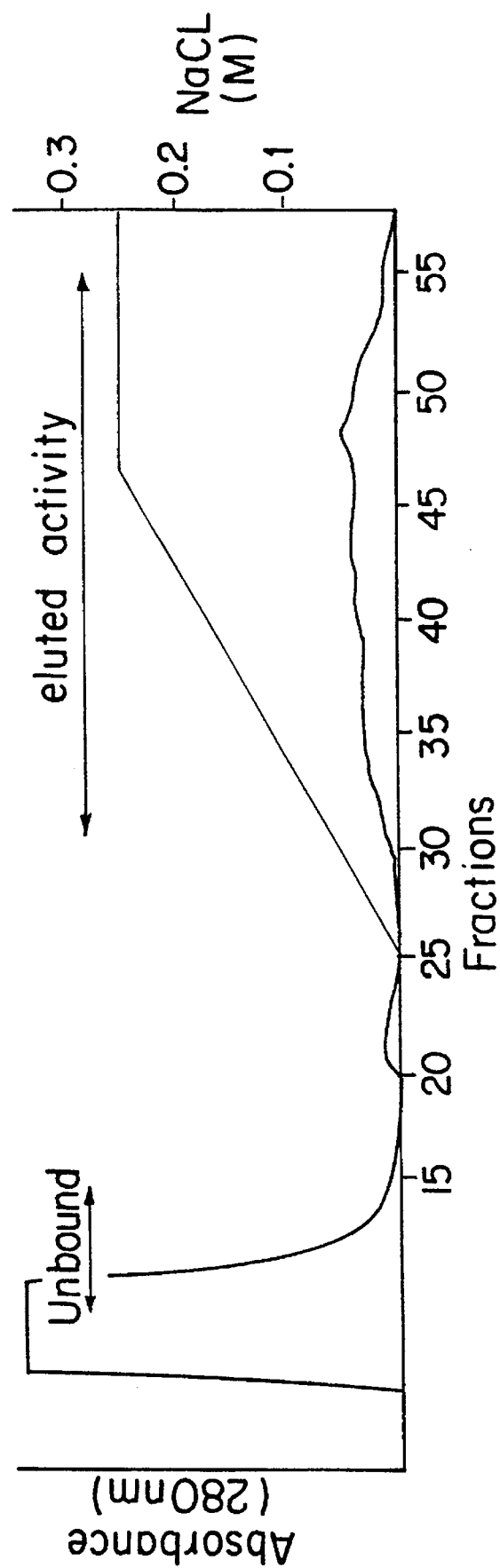
FIG. 1 depicts the elution of the recombinant chondroitinase I enzyme from a cation exchange chromatography column using a sodium chloride gradient. The method used to purify the native enzyme is used here to attempt to purify the recombinant enzyme. The initial fractions at the left do not bind to the column. They contain the majority of the chondroitinase I enzyme activity. The fractions at right containing the enzyme are marked "eluted activity". The gradient is from 0.0 to 250 mM NaCl.

Under less stringent binding conditions of pH 6.8 and 5 mM phosphate, an improvement of binding with one batch of material to 60–90% is observed. However, elution of the recombinant protein with the NaCl gradient gives al broad activity peak, rather than a sharp peak (see FIG. 1). This indicates the product is heterogeneous. Furthermore, in subsequent fermentation batches, the recombinant enzyme binds poorly (1–40%), even using the less stringent binding conditions. Most of these batches are not processed to the end, as there is poor binding. Therefore, their overall recovery is not quantified.

Based on these results, it is concluded that the recombinant chondroitinase I enzyme has a reduced basicity compared to the native enzyme, and that the basicity also varies between batches, as well as within the same batch.

It is evident that the method used to isolate and purify the native enzyme is not appropriate for the recombinant enzyme. The method produces low yields of protein at high cost. Furthermore, for large batches, large amounts of solvent waste are produced containing large amounts of a nitrogen-containing compound (ammonium sulfate). This is undesirable from an environmental point of view.

A hypothesis is then developed to explain these poor results and to provide a basis for developing improved isolation and purification methods. It is known that the native chondroitinase I enzyme is basic at neutral pH. It is therefore assumed that the surface of the enzyme has a net excess of positive charges.

Without being bound by this hypothesis, it is believed that, in recombinant expression of the enzyme, the host cell contains or produces small, negatively charged molecules. These negatively charged molecules bind to the enzyme, thereby reducing the number of positive charges on the enzyme. If these negatively charged molecules bind with high enough affinity to copurify with the enzyme, they can cause an alteration of the behavior of the enzyme on the ion exchange column.

Support for this hypothesis is provided by the data described below. In general, cation exchange resins bind to proteins better at lower pH's than higher pH's. Thus, a protein which is not very basic, and hence does not bind at a high pH, can be made to bind to the cation exchanger by carrying out the operation at a lower pH. At pH 7.2, the native enzyme binds completely to a cation exchange resin. However, the recombinant-derived enzyme, due to the lowered basicity as a result of binding of the negatively charged molecules, does not bind very well (less than 10%). This enzyme can be made to bind up to 70% by using a pH of 6.8 and a lower phosphate concentration (5 mM rather than 20 mM), but heterogeneity and low yield remain great problems. Indeed, only one fermentation results in a 70% binding level; typically, it is much less (less than 10%) even at pH 6.8. This level of binding varies dramatically between different fermentation batches.

This hypothesis and a possible solution to the problem are then tested. If negatively charged molecules are attaching non-covalently to chondroitinase I, thus decreasing its basicity, it should be possible to remove these undesired molecules by using a strong, high capacity anion exchange resin. Removal of the negatively charged molecules should then restore the basicity of the enzyme. The enzyme could then be bound to a cation exchange resin and eluted therefrom in pure form at higher yields.

Experiments demonstrate that this approach indeed provides a solution to the problem encountered with the isolation and purification of the recombinantly expressed chondroitinase I enzyme.

As is discussed below, chondroitinase I is recombinantly expressed in two forms. The enzyme is expressed with a signal peptide, which is then cleaved to produce the mature enzyme. The enzyme is also expressed without a signal peptide, to produce directly the mature enzyme. The two embodiments of this invention which will now be discussed are suitable for use in purifying either of these forms of the enzyme.

In the first embodiment of this invention, the host cells which express the recombinant chondroitinase I enzyme are lysed by homogenization to release the enzyme into the supernatant. The supernatant is then subjected to diafiltration to remove salts and other small molecules. However, this step only removes the free, but not the bound form of the negatively charged molecules. The bound form of these charged species is next removed by passing the supernatant through a strong, high capacity anion exchange resin-containing column. An example of such a resin is the Macro-Prep™ High Q resin, which contains a quaternary ammonium functional group (Bio-Rad, Melville, N.Y.). Other strong, high capacity anion exchange columns are also suitable. Weak anion exchangers containing a diethylaminoethyl (DEAE) ligand also are suitable, although they are not as effective. Similarly, low capacity resins are also suitable, although they too are not as effective. The negatively charged molecules bind to the column, while the enzyme passes through the column. It is also found that some unrelated, undesirable proteins also bind to the column.

Next, the eluate from the anion exchange column is directly loaded to a cation exchange resin-containing column. Examples of such resins are the S-Sepharose™ (Pharmacia, Piscataway, N.J.) and the Macro-Prep™ High S (Bio-Rad), which contain sulfonic acid functional groups. Each of these two resin-containing columns has $SO_3^-$ ligands bound thereto in order to facilitate the exchange of cations. Other cation exchange columns are also suitable. The enzyme binds to the column and is then eluted with a solvent capable of releasing the enzyme from the column.

Any salt which increases the conductivity of the solution is suitable for elution. Examples of such salts include sodium salts, as well as potassium salts and ammonium salts. An aqueous sodium chloride solution of appropriate concentration is suitable. A gradient, such as 0 to 250 mM sodium chloride is acceptable, as is a step elution using 200 mM sodium chloride.

Figure 2:
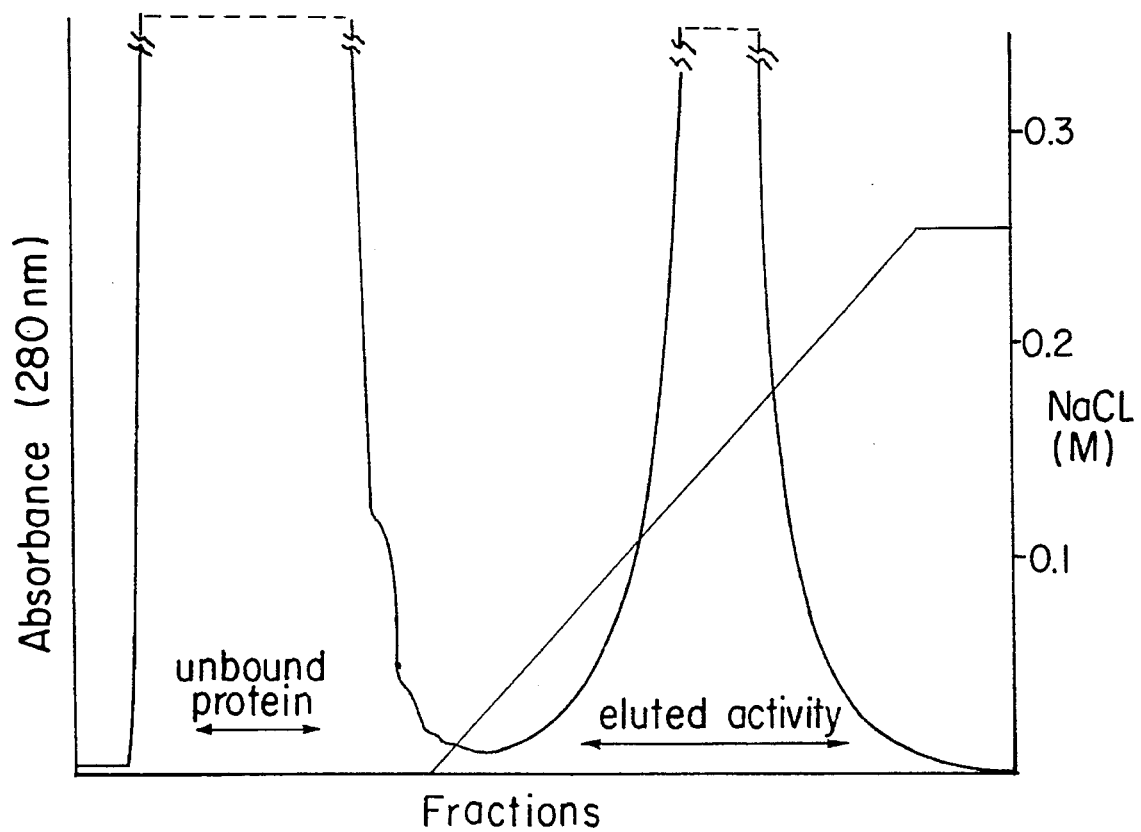
FIG. 2 depicts the elution of the recombinant chondroitinase I enzyme from a cation exchange column, after first passing the supernatant through an anion exchange column, in accordance with a method of this invention. The initial fractions at the left do not bind to the column, and contain only traces of chondroitinase I activity. The fractions at right containing the enzyme are marked "eluted activity". The gradient is from 0.0 to 250 mMNaCl.

A sharp peak is seen in the sodium chloride gradient elution (FIG. 2). The improvement in enzyme yield over the prior method is striking. The recombinant chondroitinase I enzyme is recovered at a purity of 99% at a yield of 80–90%.

The purity of the protein is measured by scanning the bands in SDS-PAGE gels. A 4–20% gradient of acrylamide is used in the development of the gels. The band(s) in each lane of the gel is scanned using the procedure described above.

These improvements are related directly to the increase in binding of the enzyme to the cation exchange column which results from first using the anion exchange column. In comparative experiments, when only the cation exchange column is used, only 1% of the enzyme binds to the column. However, when the anion exchange column is used first, over 95% of the enzyme binds to the column.

The high purity and yield obtained with the first embodiment of this invention make it more feasible to manufacture the recombinant chondroitinase I enzyme on a large scale.

In a second embodiment of this invention, two additional steps are inserted in the method before the diafiltration step of the first embodiment. The supernatant is treated with an acidic solution to precipitate out the desired enzyme. The pellet is recovered and then dissolved in an alkali solution to again place the enzyme in a basic environment. The solution is then subjected to the diafiltration and subsequent steps of the first embodiment of this invention.

In comparative experiments with the second embodiment of this invention, when only the cation exchange column is used, only 5% of the enzyme binds to the column. However, when the anion exchange column is used first, essentially 100% of the enzyme binds to the column. The second embodiment provides comparable enzyme purity and yield to the first embodiment of the invention.

Acid precipitation removes proteins that remain soluble; however, these proteins are removed anyway by the cation and anion exchange steps that follow (although smaller columns may be used). An advantage of the acid precipitation step is that the sample volume is decreased to about 20% of the original volume after dissolution, and hence can be handled more easily on a large scale. However, the additional acid precipitation and alkali dissolution steps of the second embodiment mean that the second embodiment is more time consuming than the first embodiment. On a manufacturing scale, the marginal improvements in purity and yield provided by the second embodiment may be outweighed by the simpler procedure of the first embodiment, which still provides highly pure chondroitinase I enzyme at high yields. An additional benefit of the two embodiments of the invention is that cleavage of the enzyme into 90 kD and 18 kD fragments is avoided.

Figure 3:
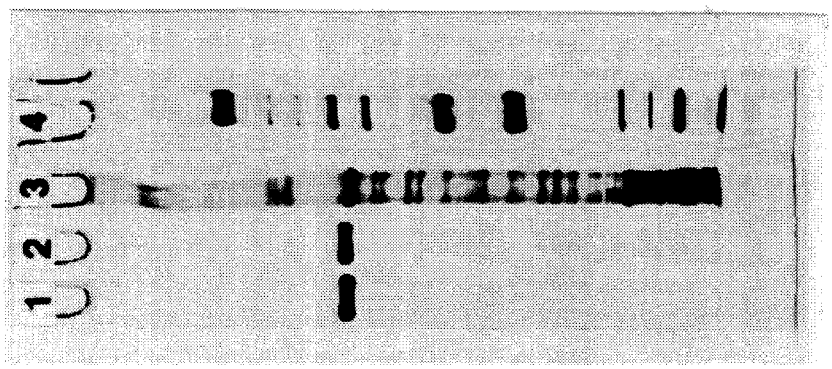
FIG. 3 depicts sodium dodecyl sulfate-polyacrylamide gel chromatography (SDS-PAGE) of the recombinant chondroitinase I enzyme before and after the purification methods of this invention are used. In the SDS-PAGE gel photograph, Lane 1 is the enzyme purified using the method of the first embodiment of the invention; Lane 2 is the enzyme purified using the method of the second embodiment of the invention; Lane 3 represents the supernatant from the host cell prior to purification—many other proteins are present; Lane 4 represents the following molecular weight standards: 14.4 kD—lysozyme; 21.5 kD—trypsin inhibitor; 31 kD—carbonic anhydrase; 42.7 kD—ovalbumin; 66.2 kD—bovine serum albumin; 97.4 kD—phosphorylase B; 116 kD—beta-galactosidase; 200 kD—myosin. A single sharp band is seen in Lanes 1 and 2.

The high purity of the enzyme produced by the two embodiments of this invention is depicted in FIG. 3. A single sharp band is seen in the SDS-PAGE gel photograph: Lane 1 is the enzyme using the method of the first embodiment; Lane 2 is the enzyme using the method of the second embodiment (Lane 3 represents the supernatant from the host cell prior to purification—many other proteins are present; Lane 4 represents molecular weight standards).

The recombinant chondroitinase I enzyme which is purified according to the method of this invention is obtained using genetic engineering techniques. For example, an EcoRI fragment is obtained which contains the gene encoding the enzyme. The DNA sequence of the fragment is 3980 nucleotides in length (SEQ ID NO:1). Translation of the DNA sequence into the putative amino acid sequence reveals a continuous open reading frame (SEQ ID NO:1, nucleotides 119–3181) encoding 1021 amino acids (SEQ ID NO:2).

In turn, analysis of the amino acid sequence reveals a 24 residue signal sequence (SEQ ID NO:2, amino acids 1–24), followed by a 997 residue mature (processed) chondroitinase I enzyme (SEQ ID NO:2, amino acids 25–1021).

The "18 kD" and "90 kD" fragments are found to be adjacent to each other, with the "18 kD" fragment constituting the first 157 amino acids of the mature protein (SEQ ID NO:2, amino acids 25–181), and the "90 kD" fragment constituting the remaining 840 amino acids of the mature protein (SEQ ID NO:2, amino acids 182–1021).

The chondroitinase I enzyme of this invention is expressed using established recombinant DNA methods. Suitable host organisms include bacteria, viruses, yeast, insect or mammalian cell lines, as well as other conventional organisms. The host cell is transformed with a plasmid containing a purified isolated DNA fragment encoding for the chondroitinase I enzyme. The host cell is then cultured under conditions which permit expression of the enzyme by the host cell. In the Examples below, an *E. coli* host cell is used. However, the isolation and purification methods of this invention are suitable for use with any of the host cell expression systems described above.

It may be desirable to subject the chondroitinase I gene to site-directed mutagenesis to introduce unique restriction sites. These permit the gene to be moved, in the correct reading frame, into an expression system which results in expression of the chondroitinase I enzyme at high levels. Such an appropriate host cell is the bacterium *E. coli*.

Two different types of mutagenized constructs are prepared. In the first, the three nucleotides immediately upstream of the initiation codon are changed (SEQ ID NO:1, nucleotides 116–118-CAT instead of ATA) through the use of a mutagenic oligonucleotide (SEQ ID NO:3). The coding region and amino acid sequence encoded by the resulting construct are not changed, and the signal sequence is preserved (SEQ ID NO:1, nucleotides 119–3181; SEQ ID NO:2).

In the second construct, the site-directed mutagenesis is carried out at the junction of the signal sequence and the start of the mature protein. A mutagenic oligonucleotide (SEQ ID NO:4) is used which differs at six nucleotides from those of the native sequence (SEQ ID NO:1, nucleotides 185–190). The sequence differences result in (a) the deletion of the signal sequence, and (b) the addition of a methionine residue at the amino-terminus, resulting in a 998 amino acid protein (SEQ ID NO:5, nucleotides 188–3181; SEQ ID NO:6).

The gene lacking the signal sequence is inserted into an appropriate expression vector. One such vector is pET-9A (5; Novagen, Madison, Wis.), which is derived from elements of the *E. coli* bacteriophage T7. The resulting recombinant plasmid is designated pTM49-6. The plasmid is then used to transform an appropriate expression host cell, such as the *E. coli* B strain BL21/(DE3)/pLysS (6,7).

Samples of this *E. coli* B strain BL21(DE3)/pLysS carrying the recombinant plasmid pTM49-6 have been deposited by Applicant's Assignee on Feb. 4, 1993, with the American Type Culture Collection, 12301 Parklawn Drive, Rockville, Md. 20852, U.S.A., and have been assigned ATCC accession number 69234.

The material deposited with the ATCC can also be used in conjunction with the Sequence Listings herein to regenerate the native chondroitinase I gene sequence (SEQ ID NO:1, nucleotides 116–118-ATA is restored), using conventional genetic engineering technology.

In the Examples below, the chondroitinase I gene lacking the signal sequence is used. However, the isolation and purification methods of this invention are equally applicable to enzyme expressed by a gene having the native nucleotide sequence, by a gene of the first site-directed mutagenesis construct described above, or by other nucleotide sequences which are biologically equivalent to the native nucleotide sequence.

Production of the native chondroitinase I enzyme in *P. vulgaris* after induction with chondroitin sulfate does not provide a high yield of enzyme; the enzyme represents approximately 0.1% of total protein present. When the recombinant construct with the signal sequence deleted is used in *E. coli*, approximately 15% of the total protein is the chondroitinase I enzyme.

Because of the virtually identical isoelectric points and similar molecular weights for the two proteins, the first method described above for isolating and purifying the recombinant chondroitinase I protein is adapted for isolating and purifying the recombinant chondroitinase II protein, and then modified as will now be described.

The need for the modification of the method is based on the fact that the recombinant chondroitinase II protein is expressed at levels approximately several-fold lower than the recombinant chondroitinase I protein; therefore, a more powerful and selective solution is necessary in order to obtain a final chondroitinase II product of a purity equivalent to that obtained for the chondroitinase I protein.

The first several steps of the method for the chondroitinase II protein are the same as those used to isolate and purify the chondroitinase I protein. Initially, the host cells which express the recombinant chondroitinase II enzyme are lysed by homogenization to release the enzyme into the supernatant. The supernatant is then subjected to diafiltration to remove salts and other small molecules. However, this step only removes the free, but not the bound form of the negatively charged molecules. The bound form of these charged species is next removed by passing the supernatant through a strong, high capacity anion exchange resin-containing column. An example of such a resin is the Macro-Prep™ High Q resin (Bio-Rad, Melville, N.Y.). Other strong, high capacity anion exchange columns are also suitable. Weak anion exchangers containing a diethylaminoethyl (DEAE) ligand also are suitable, although they are not as effective. Similarly, low capacity resins are also suitable, although they too are not as effective. The negatively charged molecules bind to the column, while the enzyme passes through the column. It is also found that some unrelated, undesirable proteins also bind to the column.

Next, the eluate from the anion exchange column is directly loaded to a cation exchange resin-containing column. Examples of such resins are the S-Sepharose™ (Pharmacia, Piscataway, N.J.) and the Macro-Prep™ High S (Bio-Rad). Each of these two resin-containing columns has $SO_3^-$ ligands bound thereto in order to facilitate the exchange of cations. Other cation exchange columns are also suitable. The enzyme binds to the column, while a significant portion of contaminating proteins elute unbound.

At this point, the method diverges from that used for the chondroitinase I protein. Instead of eluting the protein with a non-specific salt solution capable of releasing the enzyme from the cation exchange column, a specific elution using a solution containing chondroitin sulfate is used.

This procedure utilizes the affinity the positively charged chondroitinase II protein has for the negatively charged chondroitin sulfate. The affinity is larger than that accounted for by a simple positive and negative interaction alone. It is an enzyme-substrate interaction, which is similar to other specific biological interactions of high affinity, such as antigen-antibody, ligand-receptor, co-factor-protein and inhibitor/activator-protein. Hence, the chondroitin sulfate is able to elute the enzyme from the negatively charged resin. In contrast, the resin-enzyme interaction is a simple positive and negative interaction.

Although affinity elution chromatography is as easy to practice as ion-exchange chromatography, the elution is specific, unlike salt elution. Thus, it has the advantages of both affinity chromatography (specificity), as well as ion-exchange chromatography (low cost, ease of operation, reusability).

Another advantage is the low conductivity of the eluent (approximately 5% of that of the salt eluent), which allows for further ion-exchange chromatography without a diafiltration/dialysis step, which is required when a salt is used. Note, that this is not a consideration in the method for the chondroitinase I protein, because no further ion-exchange chromatography is needed in order to obtain the purified chondroitinase I protein.

There is another reason for not using the method for purifying recombinant chondroitinase I. Chondroitinase II obtained using the chondroitinase I salt elution purification method has poor stability; there is extensive degradation at 4° C. within one week. In contrast, chondroitinase II obtained by affinity elution is stable. The reason for this difference in stability is not known. It is to be noted that chondroitinase I obtained by salt elution is stable.

The cation exchange column is next washed with a phosphate buffer to elute unbound proteins, followed by washing with borate buffer to elute loosely bound contaminating proteins and to increase the pH of the resin to that required for the optimal elution of the chondroitinase II protein using the substrate, chondroitin sulfate.

Next, a solution of chondroitin sulfate in water, adjusted to pH 9.0, is used to elute the chondroitinase II protein, as a sharp peak (recovery 65%) and at a high purity of approximately 95%. A 1% concentration of chondroitin sulfate is used. A gradient of this solvent is also acceptable.

Because the chondroitin sulfate has an affinity for the chondroitinase II protein which is stronger than its affinity for the resin of the column, the chondroitin sulfate co-elutes with the protein. This ensures that only protein which recognizes chondroitin sulfate is eluted, which is desirable, but also means that an additional process step is necessary to separate the chondroitin sulfate from the chondroitinase II protein.

In this separation step, the eluate is adjusted to a neutral pH and is loaded as is onto an anion exchange resin-containing column, such as the Macro-Prep™ High Q resin. The column is washed with a phosphate buffer. The chondroitin sulfate binds to the column, while the chondroitinase II protein flows through in the unbound pool with greater than 95% recovery. At this point, the protein is pure, except for the presence of a single minor contaminant of approximately 37 kD. The contaminant may be a breakdown product of the chondroitinase II protein.

This contaminant is effectively removed by a crytallization step. The eluate from the anion exchange column is concentrated and the solution is maintained at a reduced temperature such as 4° C. for several days to crystallize out the pure chondroitinase II protein. The supernatant contains the 37 kD contaminant. Centrifugation causes the crystals to form a pellet, while the supernatant with the 37 kD contaminant is removed by pipetting. The crystals are then washed with water. The washed crystals are composed of the chondroitinase II protein at a purity of greater than 99%.

In a second embodiment of this invention for the chondroitinase II protein, two additional steps are inserted in the method before the diafiltration step of the first embodiment. The supernatant is treated with an acidic solution to precipitate out the desired enzyme. The pellet is recovered and then dissolved in an alkali solution to again place the enzyme in a basic environment. The solution is then subjected to the diafiltration and subsequent steps of the first embodiment of this invention.

Acid precipitation removes proteins that remain soluble; however, these proteins are removed anyway by the cation and anion exchange steps that follow (although smaller columns may be used). An advantage of the acid precipitation step is that the sample volume is decreased compared to the original volume after dissolution, and hence can be handled more easily on a large scale. However, the additional acid precipitation and alkali dissolution steps of the second embodiment mean that the second embodiment is more time consuming than the first embodiment. On a manufacturing scale, the marginal improvements in purity and yield provided by the second embodiment may be outweighed by the simpler procedure of the first embodiment, which still provides highly pure chondroitinase II enzyme at high yields.

The recombinant chondroitinase II enzyme which is purified according to the method of this invention is obtained using genetic engineering techniques. For example, a fragment is obtained which contains the gene encoding the enzyme. The DNA sequence of the fragment is 6519 nucleotides in length (SEQ ID NO:7). Translation of the DNA sequence into the putative amino acid sequence reveals an open reading frame (SEQ ID NO:7, nucleotides 3238–6276) encoding 1013 amino acids (SEQ ID NO:8).

In turn, analysis of the amino acid sequence reveals a 23 residue signal sequence (SEQ ID NO:8, amino acids 1–23), followed by a 990 residue mature (processed) chondroitinase II enzyme (SEQ ID NO:8, amino acids 24–1013).

The chondroitinase II enzyme of this invention is expressed using established recombinant DNA methods. Suitable host organisms include bacteria, viruses, yeast, insect or mammalian cell lines, as well as other conventional organisms. The host cell is transformed with a plasmid containing a purified isolated DNA fragment encoding for the chondroitinase II enzyme. The host cell is then cultured under conditions which permit expression of the enzyme by the host cell. In the Examples below, an *E. coli* host cell is used. However, the isolation and purification methods of this invention are suitable for use with any of the host cell expression systems described above.

The gene encoding the chondroitinase II protein is inserted into an appropriate expression vector. One such vector is pET-9A (5; Novagen, Madison, Wis.), which is derived from elements of the *E. coli* bacteriophage T7. The resulting recombinant plasmid is designated $LP^21359$. The plasmid is then used to transform an appropriate expression host cell, such as the *E. coli* B strain BL21/(DE3)/pLysS (6,7).

Samples of this *E. coli* B strain designated TD112, which is BL21(DE3)/pLysS carrying the recombinant plasmid $LP^21359$, have been deposited by Applicant's Assignee on Apr. $_{13}$, 1993, with the American Type Culture Collection, 12301 Parklawn Drive, Rockville, Md. 20852, U.S.A., and have been assigned ATCC accession number 69598.

Production of the native chondroitinase II enzyme in *P. vulgaris* after induction with chondroitin sulfate does not provide a high yield of enzyme; the enzyme represents approximately 0.1% of total protein present. When the recombinant construct is used in *E. coli*, approximately 2.5% of the total protein is the chondroitinase II enzyme.

In order that this invention may be better understood, the following examples are set forth. The examples are for the purpose of illustration only and are not to be construed as limiting the scope of the invention.

EXAMPLE 1

Method For The Isolation And Purification Of The Native Chondroitinase I Enzyme As Adapted To The Recombinant Enzyme The native enzyme is produced by fermentation of a culture of *P. vulgaris*. The bacterial cells are first recovered from the medium and resuspended in buffer. The cell suspension is then homogenized to lyse the bacterial cells. Then a charged particulate such as 50 ppm Bioacryl (Toso Haas, Philadelphia, Pa.), is added to remove DNA, aggregates and debris from the homogenization step. Next, the solution is brought to 40% saturation of ammonium sulfate to precipitate out undesired proteins. The chondroitinase I remains in solution.

The solution is then filtered using a 0.22 micron SP240 filter (Amicon, Beverly, Mass.), and the retentate is washed using nine volumes of 40% ammonium sulfate solution to recover most of the enzyme. The filtrate is concentrated and subjected to diafiltration with a sodium phosphate buffer using a 30 kD filter to remove salts and small molecules.

The filtrate containing chondroitinase I is subjected to cation exchange chromatography using a Cellufine™ cellulose sulfate column (Chisso Corporation, distributed by Amicon). At pH 7.2, 20 mM sodium phosphate, more than 98% of the chondroitinase I binds to the column. The native chondroitinase I is then eluted from the column using a 0 to 250 mM sodium chloride gradient, in 20 mM sodium phosphate buffer.

The eluted enzyme is then subjected to additional chromatography steps, such as anion exchange and hydrophobic interaction column chromatography. As a result of all of these procedures, chondroitinase I is obtained at a purity of 90–97% as measured by SDS-PAGE scanning (see above). However, the yield of the native protein is only 25–35%, determined as described above. This method also results in the cleavage of the approximately 110 kD chondroitinase I protein into a 90 kD and an 18 kD fragment. Nonetheless, the two fragments remain non-ionically bound and exhibit chondroitinase I activity.

When this procedure is repeated with lysed host cells carrying a recombinant plasmid encoding chondroitinase I, significantly poorer results are obtained. Less than 10% of the chondroitinase I binds to the cation exchange column at standard stringent conditions of pH 7.2, 20 mM sodium phosphate.

Under less stringent binding conditions of pH 6.8 and 5 mM phosphate, an improvement of binding with one batch of material to 60–90% is observed. However, elution of the recombinant protein with the NaCl gradient gives a broad activity peak, rather than a sharp peak (see FIG. 1). This indicates the product is heterogeneous. Furthermore, in subsequent fermentation batches, the recombinant enzyme binds poorly (1–40%), even using the less stringent binding conditions. Batches that bind poorly are not completely processed, so their overall recovery is not quantified.

EXAMPLE 2

First Method For The Isolation And Purification Of Recombinant Chondroitinase I According To This Invention As a first step, the host cells which express the recombinant chondroitinase I enzyme are homogenized to lyse the cells. This releases the enzyme into the supernatant.

In one embodiment of this invention, the supernatant is first subjected to diafiltration to remove salts and other small molecules. An example of a suitable filter is a spiral wound 30 kD filter made by Amicon (Beverly, Mass.). However, this step only removes the free, but not the bound form of the negatively charged molecules. The bound form of these charged species is removed by passing the supernatant through a strong, high capacity anion exchange resin-containing column. An example of such a resin is the Macro-Prep™ High Q resin (Bio-Rad, Melville, N.Y.). Other strong, high capacity anion exchange columns are also suitable. The negatively charged molecules bind to the column, while the enzyme passes through the column. It is also found that some unrelated, undesirable proteins also bind to the column.

Next, the eluate from the anion exchange column is directly loaded to a cation exchange resin-containing column. Examples of such resins are the S-Sepharose™ (Pharmacia, Piscataway, N.J.) and the Macro-Prep™ High S (Bio-Rad). Each of these two resin-containing columns has $SO_3^-$ ligands bound thereto in order to facilitate the exchange of cations. Other cation exchange columns are also suitable. The enzyme binds to the column and is then eluted with a solvent capable of releasing the enzyme from the column.

Any salt which increases the conductivity of the solution is suitable for elution. Examples of such salts include sodium salts, as well as potassium salts and ammonium salts. An aqueous sodium chloride solution of appropriate concentration is suitable. A gradient, such as 0 to 250 mM sodium chloride is acceptable, as is a step elution using 200 mM sodium chloride.

A sharp peak is seen in the sodium chloride gradient elution (FIG. 2). The improvement in enzyme yield over the prior method is striking. The recombinant chondroitinase I enzyme is recovered at a purity of 99% at a yield of 80–90%.

The purity of the protein is measured by scanning the bands in SDS-PAGE gels. A 4–20% gradient of acrylamide is used in the development of the gels. The band(s) in each lane of the gel is scanned using the procedure described above.

These improvements are related directly to the increase in binding of the enzyme to the cation exchange column which results from first using the anion exchange column. In comparative experiments, when only the cation exchange column is used, only 1% of the enzyme binds to the column. However, when the anion exchange column is used first, over 95% of the enzyme binds to the column.

EXAMPLE 3

Second Method For The Isolation And Purification Of Recombinant Chondroitinase I According To This Invention In the second embodiment of this invention, two additional steps are inserted in the method before the diafiltration step of the first embodiment. The supernatant is treated with an acidic solution, such as 1M acetic acid, bringing the supernatant to a final pH of 4.5, to precipitate out the desired enzyme. The pellet is obtained by centrifugation at 5,000×g for 20 minutes. The pellet is then dissolved in an alkali solution, such as 20–30 mM NaOH, bringing it to a final pH of 9.8. The solution is then subjected to the diafiltration and subsequent steps of the first embodiment of this invention.

In comparative experiments with the second embodiment of this invention, when only the cation exchange column is used, only 5% of the enzyme binds to the column. However, when the anion exchange column is used first, essentially 100% of the enzyme binds to the column. The second embodiment provides comparable enzyme purity and yield to the first embodiment of the invention.

Acid precipitation removes proteins that remain soluble; however, these proteins are removed anyway by the cation and anion exchange steps that follow (although smaller columns may be used). An advantage of the acid precipitation step is that the sample volume is decreased to about 20% of the original volume after dissolution, and hence can be handled more easily on a large scale. However, the additional acid precipitation and alkali dissolution steps of the second embodiment mean that the second embodiment is more time consuming than the first embodiment. On a manufacturing scale, the marginal improvements in purity and yield provided by the second embodiment may be outweighed by the simpler procedure of the first embodiment, which still provides highly pure enzyme at high yields.

The high purity of the recombinant enzyme obtained by the two embodiments of this invention is depicted in FIG. 3. A single sharp band is seen in the SDS-PAGE gel photograph: Lane 1 is the enzyme using the method of the first embodiment; Lane 2 is the enzyme using the method of the second embodiment; Lane 3 represents the supernatant from the host cell prior to purification—many other proteins are present; and Lane 4 represents molecular weight standards.

EXAMPLE 4

First Method For The Isolation And Purification Of Recombinant Chondroitinase II According To This Invention The initial part of this method is the same as that used for the recombinant chondroitinase I enzyme. As a first step, the host cells which express the recombinant chondroitinase II enzyme are homogenized to lyse the cells. This releases the enzyme into the supernatant.

In one embodiment of this invention, the supernatant is first subjected to diafiltration to remove salts and other small molecules. An example of a suitable filter is a spiral wound 30 kD filter made by Amicon (Beverly, Mass.). However, this step only removes the free, but not the bound form of the negatively charged molecules. The bound form of these charged species is removed by passing the supernatant (see the SDS-PAGE gel depicted in FIG. 4, lane 1) through a strong, high capacity anion exchange resin-containing column. An example of such a resin is the Macro-Prep™ High Q resin (Bio-Rad, Melville, N.Y.). Other strong, high capacity anion exchange columns are also suitable. The negatively charged molecules bind to the column, while the enzyme passes through the column with approximately 90% recovery of the enzyme. It is also found that some unrelated, undesirable proteins also bind to the column.

Next, the eluate from the anion exchange column (FIG. 4, lane 2) is directly loaded to a cation exchange resin-containing column. Examples of such resins are the S-Sepharose™ (Pharmacia, Piscataway, N.J.) and the Macro-Prep™ High S (Bio-Rad). Each of these two resin-containing columns has $SO_3^-$ ligands bound thereto in order to facilitate the exchange of cations. Other cation exchange columns are also suitable. The enzyme binds to the column, while a significant portion of contaminating proteins elute unbound.

At this point, the method diverges from that used for the chondroitinase I protein. Instead of eluting the protein with a non-specific salt solution capable of releasing the enzyme from the cation exchange column, a specific elution using a solution containing chondroitin sulfate is used. A 1% concentration of chondroitin sulfate is used; however, a gradient of this solvent is also acceptable. The specific chondroitin sulfate solution is preferred to the non-specific salt solution because the recombinant chondroitinase II protein is expressed at levels approximately several-fold lower than the recombinant chondroitinase I protein; therefore, a more powerful and selective solution is necessary in order to obtain a final chondroitinase II product of a purity equivalent to that obtained for the chondroitinase I protein.

The cation exchange column is next washed with a phosphate buffer, pH 7.0, to elute unbound proteins, followed by washing with borate buffer, pH 8.5, to elute loosely bound contaminating proteins and to increase the pH of the resin to that required for the optimal elution of the chondroitinase II protein using the substrate, chondroitin sulfate.

Figure 4:
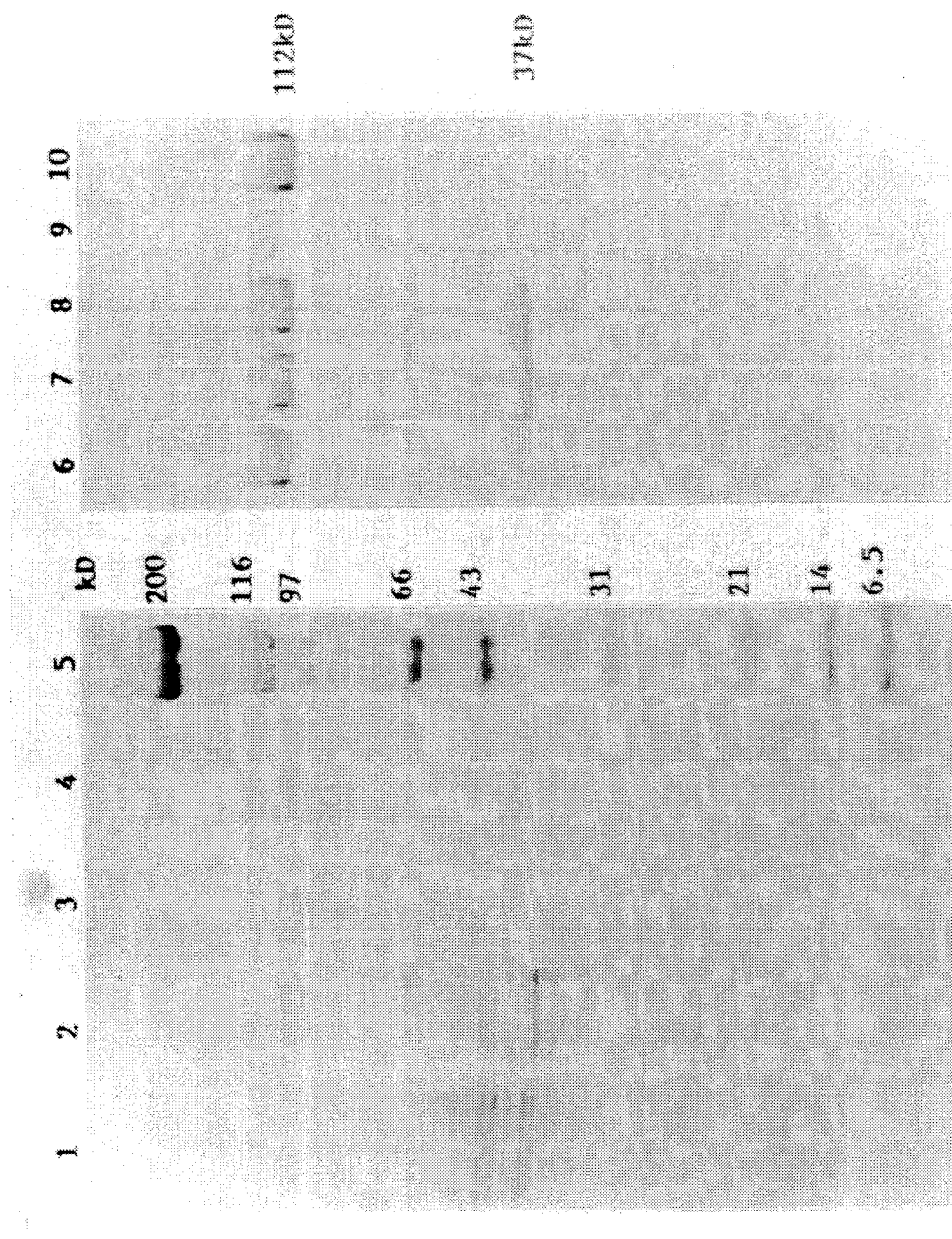
FIG. 4 depicts SDS-PAGE chromatography of the recombinant chondroitinase II enzyme during various stages of purification using a method of this invention. In the SDS-PAGE gel photograph, Lane 1 is the crude supernatant after diafiltration; Lane 2 the eluate after passage of the supernatant through an anion exchange resin-containing column; Lane 3 is the enzyme after elution through a cation exchange resin-containing column; Lane 4 is the enzyme after elution through a second anion exchange resin-containing column; Lane 5 represents the same molecular weight standards as described for FIG. 3, plus 6.5 kD—aprotinin; Lane 6 is the same as Lane 4, except it is overloaded to show the approximately 37 kD contaminant; Lane 7 is the 37 kD contaminant in the supernatant after crystallization of the chondroitinase II enzyme; Lane 8 is first wash of the crystals; Lane 9 is the second wash of the crystals; Lane 10 is the enzyme in the washed crystals after redissolving in water.

Next, a 1% solution of chondroitin sulfate in water, adjusted to pH 9.0, is used to elute the chondroitinase II protein, as a sharp peak (recovery 65%) and at a high purity of approximately 95% (FIG. 4, lane 3). However, the chondroitin sulfate has an affinity for the chondroitinase II protein which is stronger than its affinity for the resin of the column, and therefore the chondroitin sulfate co-elutes with the protein. This ensures that only protein which recognizes chondroitin sulfate is eluted, which is desirable, but also means that an additional process step is necessary to separate the chondroitin sulfate from the chondroitinase II protein.

In this separation step, the eluate is adjusted to pH 7.0 and is loaded as is onto an anion exchange resin-containing column, such as the Macro-Prep™ High Q resin. The column is washed with a 20 mM phosphate buffer, pH 6.8. The chondroitin sulfate binds to the column, while the chondroitinase II protein flows through in the unbound pool with greater than 95% recovery. At this point, the protein is pure, except for the presence of a single minor contaminant of approximately 37 kD (FIG. 4, lanes 4 and 6). The contaminant may be a breakdown product of the chondroitinase II protein.

This contaminant is effectively removed by a crytallization step. The eluate from the anion exchange column is concentrated to 15 mg/ml protein using an Amicon stirred cell with a 30 kD cutoff. The solution is maintained at 4° C. for several days to crystallize out the pure chondroitinase II protein. The supernatant contains the 37 kD contaminant (FIG. 4, lane 7). Centrifugation causes the crystals to form a pellet, while the supernatant with the 37 kD contaminant is removed by pipetting, and the crystals washed twice with water. After the first wash, some of the contaminant remains (FIG. 4, lane 8), but after the second wash, only the chondroitinase II protein is visible (FIG. 4, lane 9). The washed crystals are redissolved in water and exhibit a single protein band on SDS-PAGE, with a purity of greater than 99% (FIG. 4, lane 10).

EXAMPLE 5

Second Method For The Isolation And Purification Of Recombinant Chondroitinase II According To This Invention In the second embodiment of this invention, two additional steps are inserted in the method for purifying the chondroitinase II enzyme before the diafiltration step of the first embodiment. The supernatant is treated with an acidic solution, such as 1M acetic acid, bringing the supernatant to a final pH of 4.5, to precipitate out the desired enzyme. The pellet is obtained by centrifugation at 5,000×g for 20 minutes. The pellet is then dissolved in an alkali solution, such as 20–30 mM NaOH, bringing it to a final pH of 9.8. The solution is then subjected to the diafiltration and subsequent steps of the first embodiment of this invention.

Bibliography

1. Yamagata, T., et al., *J. Biol. Chem.*, 243, 1523–1535 (1968).
2. Kikuchi, H., et al., U.S. Pat. No. 5,198,355.
3. Brown, M. D., U.S. Pat. No. 4,696,816.
4. Hageman, G. S., U.S. Pat. No. 5,292,509.
5. Studier, F. W., et al., *Methods in Enzymology*, 185, 60–89 (1990).
6. Studier, F. W., and Moffatt, B. A., *J. Mol. Biol.*, 189, 113–130 (1986).
7. Moffatt, B. A., and Studier, F. W., *Cell*, 49, 221–227 (1987).

What is claimed is:

1. A method for the isolation and purification of the recombinant chondroitinase I enzyme of *Proteus vulgaris* from *E. coli* host cells, said method comprising the steps of:
   (a) lysing by homogenization the host cells to release the enzyme into the supernatant;
   (b) subjecting the supernatant to diafiltration to remove salts and other small molecules;
   (c) passing the supernatant through an anion exchange resin-containing column to produce an eluate containing the enzyme that has not bound to the column;
   (d) loading the eluate from step (c) to a cation exchange resin-containing column so that the enzyme in the eluate binds to the cation exchange column; and
   (e) treating the cation exchange column to which the enzyme has bound with a solvent that releases the enzyme from the column, producing an eluate containing the purified enzyme.

2. The method of claim 1, wherein the anion exchange column in step (c) contains a resin comprising a quaternary ammonium functional group.

3. The method of claim 1, wherein the cation exchange column in step (d) has $SO_3^-$ ligands bound therto.

4. The method of claim 3, wherein the cation exchange column of step (d) contains a resin comprising a sulfonic acid functional group.

5. The method of claim 1, wherein the solvent of step (e) is an aqueous salt solution.

6. The method of claim 5, wherein the aqueous salt solution contains a salt selected from the group consisting of sodium salts, ammonium salts and potassium salts.

7. The method of claim 6, wherein the salt is sodium chloride.

8. The method of claim 5, wherein the aqueous salt solution is eluted using a gradient.

9. The method of claim 1, wherein prior to step (b), the following two steps are performed:
   (1) treating the supernatant with an acidic solution to precipitate out the enzyme; and
   (2) recovering the pellet and then dissolving it in an alkali solution to again place the enzyme in a basic environment.

10. The method of claim 9, wherein the acidic solution in step (1) is a 1M acetic acid solution brought to a final pH of 4.5.

11. The method of claim 10, wherein the alkali solution in step (2) is a NaOH solution brought to a final pH of 9.8.

12. A method for the isolation and purification of the recombinant chondroitinase II enyzme of *Proteus vulgaris* from *E. coli* host cells, said method comprising the steps of:

(a) lysing by homogenization the host cells to release the enzyme into the supernatant;

(b) subjecting the supernatant to diafiltration to remove salts and other small molecules;

(c) passing the supernatant through an anion exchange resin-containing column to produce an eluate containing the enzyme that has not bound to the column;

(d) loading the eluate from step (c) to a cation exchange resin-containing column so that the enzyme in the eluate binds to the cation exchange column;

(e) contacting the cation exchange column with a solution of chondroitin sulfate, to produce an eluate containing the enzyme co-eluted with the chondroitin sulfate;

(f) loading the eluate from step (e) to an anion exchange resin-containing column in a solvent such that the chondroitin sulfate binds to the column, to produce an eluate containing the enzyme that has not bound to the column; and (g) concentrating the eluate from step (f) by crystallizing out the enzyme from the eluate to produce crystals and a supernatant, wherein said crystals contain the purified enzyme and said supernatant contains an approximately 37 kD contaminant.

13. The method of claim 12, wherein the anion exchange column in step (c) contains a resin comprising a quaternary ammonium functional group.

14. The method of claim 12, wherein the cation exchange column in step (d) has $SO_3^-$ ligands bound thereto.

15. The method of claim 14, wherein the cation exchange column of step (d) contains a resin comprising a sulfonic acid functional group.

16. The method of claim 12, wherein the chondroitin sulfate solution of step (e) is a concentrated solution or a gradient thereof.

17. The method of claim 16, wherein a 1% solution of chondroitin sulfate is used.

18. The method of claim 12, wherein the anion exhchange column of step (f) contains a Macro-Prep™ High Q resin.

19. The method of claim 18, wherein the solvent of step (f) is a phosphate buffer.

20. The method of claim 19, wherein the phosphate buffer is a 20 mM phosphate buffer, pH 6.8.

21. The method of claim 12, wherein the crystallization step (g) is carried out at 4° C.

22. The method of claim 12, wherein prior to step (b), the following two steps are performed:

(1) treating the supernatant with an acidic solution to precipitate out the enzyme; and (2) recovering the pellet and then dissolving it in an alkali solution to again place the enzyme in a basic environment.

23. The method of claim 22, wherein the acidic solution in step (1) is a 1M acetic acid solution brought to a final pH of 4.5.

24. The method of claim 22, wherein the alkali solution in step (2) is a NaOH solution brought to a final pH of 9.8.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
  ( A ) LENGTH: 3980 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
  ( A ) NAME/KEY: CDS
  ( B ) LOCATION: 119..3181

( x i ) SEQUENCE DESCRIPTION: SEQ ID NO:1:

```
GGAATTCCAT CACTCAATCA TTAAATTTAG GCACAACGAT GGGCTATCAG CGTTATGACA        60

AATTTAATGA AGGACGCATT GGTTTCACTG TTAGCCAGCG TTTCTAAGGA GAAAAATA         118

ATG CCG ATA TTT CGT TTT ACT GCA CTT GCA ATG ACA TTG GGG CTA TTA         166
Met Pro Ile Phe Arg Phe Thr Ala Leu Ala Met Thr Leu Gly Leu Leu
  1               5                  10                  15

TCA GCG CCT TAT AAC GCG ATG GCA GCC ACC AGC AAT CCT GCA TTT GAT         214
Ser Ala Pro Tyr Asn Ala Met Ala Ala Thr Ser Asn Pro Ala Phe Asp
             20                  25                  30

CCT AAA AAT CTG ATG CAG TCA GAA ATT TAC CAT TTT GCA CAA AAT AAC         262
Pro Lys Asn Leu Met Gln Ser Glu Ile Tyr His Phe Ala Gln Asn Asn
         35                  40                  45

CCA TTA GCA GAC TTC TCA TCA GAT AAA AAC TCA ATA CTA ACG TTA TCT         310
Pro Leu Ala Asp Phe Ser Ser Asp Lys Asn Ser Ile Leu Thr Leu Ser
     50                  55                  60

GAT AAA CGT AGC ATT ATG GGA AAC CAA TCT CTT TTA TGG AAA TGG AAA         358
Asp Lys Arg Ser Ile Met Gly Asn Gln Ser Leu Leu Trp Lys Trp Lys
 65                  70                  75                  80

GGT GGT AGT AGC TTT ACT TTA CAT AAA AAA CTG ATT GTC CCC ACC GAT         406
Gly Gly Ser Ser Phe Thr Leu His Lys Lys Leu Ile Val Pro Thr Asp
                 85                  90                  95

AAA GAA GCA TCT AAA GCA TGG GGA CGC TCA TCT ACC CCC GTT TTC TCA         454
Lys Glu Ala Ser Lys Ala Trp Gly Arg Ser Ser Thr Pro Val Phe Ser
            100                 105                 110

TTT TGG CTT TAC AAT GAA AAA CCG ATT GAT GGT TAT CTT ACT ATC GAT         502
Phe Trp Leu Tyr Asn Glu Lys Pro Ile Asp Gly Tyr Leu Thr Ile Asp
        115                 120                 125

TTC GGA GAA AAA CTC ATT TCA ACC AGT GAG GCT CAG GCA GGC TTT AAA         550
Phe Gly Glu Lys Leu Ile Ser Thr Ser Glu Ala Gln Ala Gly Phe Lys
    130                 135                 140

GTA AAA TTA GAT TTC ACT GGC TGG CGT GCT GTG GGA GTC TCT TTA AAT         598
Val Lys Leu Asp Phe Thr Gly Trp Arg Ala Val Gly Val Ser Leu Asn
145                 150                 155                 160

AAC GAT CTT GAA AAT CGA GAG ATG ACC TTA AAT GCA ACC AAT ACC TCC         646
Asn Asp Leu Glu Asn Arg Glu Met Thr Leu Asn Ala Thr Asn Thr Ser
                165                 170                 175

TCT GAT GGT ACT CAA GAC AGC ATT GGG CGT TCT TTA GGT GCT AAA GTC         694
Ser Asp Gly Thr Gln Asp Ser Ile Gly Arg Ser Leu Gly Ala Lys Val
            180                 185                 190

GAT AGT ATT CGT TTT AAA GCG CCT TCT AAT GTG AGT CAG GGT GAA ATC         742
Asp Ser Ile Arg Phe Lys Ala Pro Ser Asn Val Ser Gln Gly Glu Ile
        195                 200                 205

TAT ATC GAC CGT ATT ATG TTT TCT GTC GAT GAT GCT CGC TAC CAA TGG         790
Tyr Ile Asp Arg Ile Met Phe Ser Val Asp Asp Ala Arg Tyr Gln Trp
    210                 215                 220

TCT GAT TAT CAA GTA AAA ACT CGC TTA TCA GAA CCT GAA ATT CAA TTT         838
Ser Asp Tyr Gln Val Lys Thr Arg Leu Ser Glu Pro Glu Ile Gln Phe
```

|  |  |  |  |  |  |  |  |  |  |  |  |
|---|---|---|---|---|---|---|---|---|---|---|---|
| 225 |  |  |  | 230 |  |  |  | 235 |  |  | 240 |
| CAC | AAC | GTA | AAG | CCA | CAA | CTA | CCT | GTA | ACA | CCT | GAA | AAT | TTA | GCG | GCC | 886 |
| His | Asn | Val | Lys | Pro | Gln | Leu | Pro | Val | Thr | Pro | Glu | Asn | Leu | Ala | Ala |
|  |  |  | 245 |  |  |  | 250 |  |  |  | 255 |
| ATT | GAT | CTT | ATT | CGC | CAA | CGT | CTA | ATT | AAT | GAA | TTT | GTC | GGA | GGT | GAA | 934 |
| Ile | Asp | Leu | Ile | Arg | Gln | Arg | Leu | Ile | Asn | Glu | Phe | Val | Gly | Gly | Glu |
|  |  |  | 260 |  |  |  | 265 |  |  |  | 270 |
| AAA | GAG | ACA | AAC | CTC | GCA | TTA | GAA | GAG | AAT | ATC | AGC | AAA | TTA | AAA | AGT | 982 |
| Lys | Glu | Thr | Asn | Leu | Ala | Leu | Glu | Glu | Asn | Ile | Ser | Lys | Leu | Lys | Ser |
|  |  | 275 |  |  |  | 280 |  |  |  | 285 |
| GAT | TTC | GAT | GCT | CTT | AAT | ATT | CAC | ACT | TTA | GCA | AAT | GGT | GGA | ACG | CAA | 1030 |
| Asp | Phe | Asp | Ala | Leu | Asn | Ile | His | Thr | Leu | Ala | Asn | Gly | Gly | Thr | Gln |
|  | 290 |  |  |  | 295 |  |  |  | 300 |
| GGC | AGA | CAT | CTG | ATC | ACT | GAT | AAA | CAA | ATC | ATT | TAT | CAA | CCA | GAG | 1078 |
| Gly | Arg | His | Leu | Ile | Thr | Asp | Lys | Gln | Ile | Ile | Ile | Tyr | Gln | Pro | Glu |
| 305 |  |  |  | 310 |  |  |  | 315 |  |  |  | 320 |
| AAT | CTT | AAC | TCC | CAA | GAT | AAA | CAA | CTA | TTT | GAT | AAT | TAT | GTT | ATT | TTA | 1126 |
| Asn | Leu | Asn | Ser | Gln | Asp | Lys | Gln | Leu | Phe | Asp | Asn | Tyr | Val | Ile | Leu |
|  |  |  | 325 |  |  |  | 330 |  |  |  | 335 |
| GGT | AAT | TAC | ACG | ACA | TTA | ATG | TTT | AAT | ATT | AGC | CGT | GCT | TAT | GTG | CTG | 1174 |
| Gly | Asn | Tyr | Thr | Thr | Leu | Met | Phe | Asn | Ile | Ser | Arg | Ala | Tyr | Val | Leu |
|  |  |  | 340 |  |  |  | 345 |  |  |  | 350 |
| GAA | AAA | GAT | CCC | ACA | CAA | AAG | GCG | CAA | CTA | AAG | CAG | ATG | TAC | TTA | TTA | 1222 |
| Glu | Lys | Asp | Pro | Thr | Gln | Lys | Ala | Gln | Leu | Lys | Gln | Met | Tyr | Leu | Leu |
|  |  | 355 |  |  |  | 360 |  |  |  | 365 |
| ATG | ACA | AAG | CAT | TTA | TTA | GAT | CAA | GGC | TTT | GTT | AAA | GGG | AGT | GCT | TTA | 1270 |
| Met | Thr | Lys | His | Leu | Leu | Asp | Gln | Gly | Phe | Val | Lys | Gly | Ser | Ala | Leu |
|  | 370 |  |  |  | 375 |  |  |  | 380 |
| GTG | ACA | ACC | CAT | CAC | TGG | GGA | TAC | AGT | TCT | CGT | TGG | TGG | TAT | ATT | TCC | 1318 |
| Val | Thr | Thr | His | His | Trp | Gly | Tyr | Ser | Ser | Arg | Trp | Trp | Tyr | Ile | Ser |
| 385 |  |  |  | 390 |  |  |  | 395 |  |  |  | 400 |
| ACG | TTA | TTA | ATG | TCT | GAT | GCA | CTA | AAA | GAA | GCG | AAC | CTA | CAA | ACT | CAA | 1366 |
| Thr | Leu | Leu | Met | Ser | Asp | Ala | Leu | Lys | Glu | Ala | Asn | Leu | Gln | Thr | Gln |
|  |  |  | 405 |  |  |  | 410 |  |  |  | 415 |
| GTT | TAT | GAT | TCA | TTA | CTG | TGG | TAT | TCA | CGT | GAG | TTT | AAA | AGT | AGT | TTT | 1414 |
| Val | Tyr | Asp | Ser | Leu | Leu | Trp | Tyr | Ser | Arg | Glu | Phe | Lys | Ser | Ser | Phe |
|  |  |  | 420 |  |  |  | 425 |  |  |  | 430 |
| GAT | ATG | AAA | GTA | AGT | GCT | GAT | AGC | TCT | GAT | CTA | GAT | TAT | TTC | AAT | ACC | 1462 |
| Asp | Met | Lys | Val | Ser | Ala | Asp | Ser | Ser | Asp | Leu | Asp | Tyr | Phe | Asn | Thr |
|  |  | 435 |  |  |  | 440 |  |  |  | 445 |
| TTA | TCT | CGC | CAA | CAT | TTA | GCC | TTA | TTA | CTA | GAG | CCT | GAT | GAT | CAA | 1510 |
| Leu | Ser | Arg | Gln | His | Leu | Ala | Leu | Leu | Leu | Glu | Pro | Asp | Asp | Gln |
| 450 |  |  |  | 455 |  |  |  | 460 |
| AAG | CGT | ATC | AAC | TTA | GTT | AAT | ACT | TTC | AGC | CAT | TAT | ATC | ACT | GGC | GCA | 1558 |
| Lys | Arg | Ile | Asn | Leu | Val | Asn | Thr | Phe | Ser | His | Tyr | Ile | Thr | Gly | Ala |
| 465 |  |  |  | 470 |  |  |  | 475 |  |  |  | 480 |
| TTA | ACG | CAA | GTG | CCA | CCG | GGT | GGT | AAA | GAT | GGT | TTA | CGC | CCT | GAT | GGT | 1606 |
| Leu | Thr | Gln | Val | Pro | Pro | Gly | Gly | Lys | Asp | Gly | Leu | Arg | Pro | Asp | Gly |
|  |  |  | 485 |  |  |  | 490 |  |  |  | 495 |
| ACA | GCA | TGG | CGA | CAT | GAA | GGC | AAC | TAT | CCG | GGC | TAC | TCT | TTC | CCA | GCC | 1654 |
| Thr | Ala | Trp | Arg | His | Glu | Gly | Asn | Tyr | Pro | Gly | Tyr | Ser | Phe | Pro | Ala |
|  |  | 500 |  |  |  | 505 |  |  |  | 510 |
| TTT | AAA | AAT | GCC | TCT | CAG | CTT | ATT | TAT | TTA | TTA | CGC | GAT | ACA | CCA | TTT | 1702 |
| Phe | Lys | Asn | Ala | Ser | Gln | Leu | Ile | Tyr | Leu | Leu | Arg | Asp | Thr | Pro | Phe |
|  |  | 515 |  |  |  | 520 |  |  |  | 525 |
| TCA | GTG | GGT | GAA | AGT | GGT | TGG | AAT | AAC | CTG | AAA | AAA | GCG | ATG | GTT | TCA | 1750 |
| Ser | Val | Gly | Glu | Ser | Gly | Trp | Asn | Asn | Leu | Lys | Lys | Ala | Met | Val | Ser |
|  | 530 |  |  |  | 535 |  |  |  | 540 |
| GCG | TGG | ATC | TAC | AGT | AAT | CCA | GAA | GTT | GGA | TTA | CCG | CTT | GCA | GGA | AGA | 1798 |
| Ala | Trp | Ile | Tyr | Ser | Asn | Pro | Glu | Val | Gly | Leu | Pro | Leu | Ala | Gly | Arg |

```
545                           550                           555                           560
CAC  CCT  TTT  AAC  TCA  CCT  TCG  TTA  AAA  TCA  GTC  GCT  CAA  GGC  TAT  TAC       1846
His  Pro  Phe  Asn  Ser  Pro  Ser  Leu  Lys  Ser  Val  Ala  Gln  Gly  Tyr  Tyr
               565                 570                           575

TGG  CTT  GCC  ATG  TCT  GCA  AAA  TCA  TCG  CCT  GAT  AAA  ACA  CTT  GCA  TCT       1894
Trp  Leu  Ala  Met  Ser  Ala  Lys  Ser  Ser  Pro  Asp  Lys  Thr  Leu  Ala  Ser
               580                 585                           590

ATT  TAT  CTT  GCG  ATT  AGT  GAT  AAA  ACA  CAA  AAT  GAA  TCA  ACT  GCT  ATT       1942
Ile  Tyr  Leu  Ala  Ile  Ser  Asp  Lys  Thr  Gln  Asn  Glu  Ser  Thr  Ala  Ile
               595                 600                           605

TTT  GGA  GAA  ACT  ATT  ACA  CCA  GCG  TCT  TTA  CCT  CAA  GGT  TTC  TAT  GCC       1990
Phe  Gly  Glu  Thr  Ile  Thr  Pro  Ala  Ser  Leu  Pro  Gln  Gly  Phe  Tyr  Ala
     610                      615                      620

TTT  AAT  GGC  GGT  GCT  TTT  GGT  ATT  CAT  CGT  TGG  CAA  GAT  AAA  ATG  GTG       2038
Phe  Asn  Gly  Gly  Ala  Phe  Gly  Ile  His  Arg  Trp  Gln  Asp  Lys  Met  Val
625                      630                      635                           640

ACA  CTG  AAA  GCT  TAT  AAC  ACC  AAT  GTT  TGG  TCA  TCT  GAA  ATT  TAT  AAC       2086
Thr  Leu  Lys  Ala  Tyr  Asn  Thr  Asn  Val  Trp  Ser  Ser  Glu  Ile  Tyr  Asn
               645                 650                           655

AAA  GAT  AAC  CGT  TAT  GGC  CGT  TAC  CAA  AGT  CAT  GGT  GTC  GCT  CAA  ATA       2134
Lys  Asp  Asn  Arg  Tyr  Gly  Arg  Tyr  Gln  Ser  His  Gly  Val  Ala  Gln  Ile
               660                 665                           670

GTG  AGT  AAT  GGC  TCG  CAG  CTT  TCA  CAG  GGC  TAT  CAG  CAA  GAA  GGT  TGG       2182
Val  Ser  Asn  Gly  Ser  Gln  Leu  Ser  Gln  Gly  Tyr  Gln  Gln  Glu  Gly  Trp
               675                 680                           685

GAT  TGG  AAT  AGA  ATG  CAA  GGG  GCA  ACC  ACT  ATT  CAC  CTT  CCT  CTT  AAA       2230
Asp  Trp  Asn  Arg  Met  Gln  Gly  Ala  Thr  Thr  Ile  His  Leu  Pro  Leu  Lys
     690                      695                      700

GAC  TTA  GAC  AGT  CCT  AAA  CCT  CAT  ACC  TTA  ATG  CAA  CGT  GGA  GAG  CGT       2278
Asp  Leu  Asp  Ser  Pro  Lys  Pro  His  Thr  Leu  Met  Gln  Arg  Gly  Glu  Arg
705                      710                      715                           720

GGA  TTT  AGC  GGA  ACA  TCA  TCC  CTT  GAA  GGT  CAA  TAT  GGC  ATG  ATG  GCA       2326
Gly  Phe  Ser  Gly  Thr  Ser  Ser  Leu  Glu  Gly  Gln  Tyr  Gly  Met  Met  Ala
               725                 730                           735

TTC  GAT  CTT  ATT  TAT  CCC  GCC  AAT  CTT  GAG  CGT  TTT  GAT  CCT  AAT  TTC       2374
Phe  Asp  Leu  Ile  Tyr  Pro  Ala  Asn  Leu  Glu  Arg  Phe  Asp  Pro  Asn  Phe
               740                 745                           750

ACT  GCG  AAA  AAG  AGT  GTA  TTA  GCC  GCT  GAT  AAT  CAC  TTA  ATT  TTT  ATT       2422
Thr  Ala  Lys  Lys  Ser  Val  Leu  Ala  Ala  Asp  Asn  His  Leu  Ile  Phe  Ile
               755                 760                           765

GGT  AGC  AAT  ATA  AAT  AGT  AGT  GAT  AAA  AAT  AAA  AAT  GTT  GAA  ACG  ACC       2470
Gly  Ser  Asn  Ile  Asn  Ser  Ser  Asp  Lys  Asn  Lys  Asn  Val  Glu  Thr  Thr
               770                 775                           780

TTA  TTC  CAA  CAT  GCC  ATT  ACT  CCA  ACA  TTA  AAT  ACC  CTT  TGG  ATT  AAT       2518
Leu  Phe  Gln  His  Ala  Ile  Thr  Pro  Thr  Leu  Asn  Thr  Leu  Trp  Ile  Asn
785                      790                      795                           800

GGA  CAA  AAG  ATA  GAA  AAC  ATG  CCT  TAT  CAA  ACA  ACA  CTT  CAA  CAA  GGT       2566
Gly  Gln  Lys  Ile  Glu  Asn  Met  Pro  Tyr  Gln  Thr  Thr  Leu  Gln  Gln  Gly
               805                 810                           815

GAT  TGG  TTA  ATT  GAT  AGC  AAT  GGC  AAT  GGT  TAC  TTA  ATT  ACT  CAA  GCA       2614
Asp  Trp  Leu  Ile  Asp  Ser  Asn  Gly  Asn  Gly  Tyr  Leu  Ile  Thr  Gln  Ala
               820                 825                           830

GAA  AAA  GTA  AAT  GTA  AGT  CGC  CAA  CAT  CAG  GTT  TCA  GCG  GAA  AAT  AAA       2662
Glu  Lys  Val  Asn  Val  Ser  Arg  Gln  His  Gln  Val  Ser  Ala  Glu  Asn  Lys
               835                 840                           845

AAT  CGC  CAA  CCG  ACA  GAA  GGA  AAC  TTT  AGC  TCG  GCA  TGG  ATC  GAT  CAC       2710
Asn  Arg  Gln  Pro  Thr  Glu  Gly  Asn  Phe  Ser  Ser  Ala  Trp  Ile  Asp  His
850                      855                      860

AGC  ACT  CGC  CCC  AAA  GAT  GCC  AGT  TAT  GAG  TAT  ATG  GTC  TTT  TTA  GAT       2758
Ser  Thr  Arg  Pro  Lys  Asp  Ala  Ser  Tyr  Glu  Tyr  Met  Val  Phe  Leu  Asp
```

| | | | | | | | | | | | | | | | | |
|---|---|---|---|---|---|---|---|---|---|---|---|---|---|---|---|---|
| 865 | | | | | 870 | | | | | 875 | | | | | 880 | |
| GCG | ACA | CCT | GAA | AAA | ATG | GGA | GAG | ATG | GCA | CAA | AAA | TTC | CGT | GAA | AAT | 2806 |
| Ala | Thr | Pro | Glu | Lys 885 | Met | Gly | Glu | Met | Ala 890 | Gln | Lys | Phe | Arg | Glu 895 | Asn | |
| AAT | GGG | TTA | TAT | CAG | GTT | CTT | CGT | AAG | GAT | AAA | GAC | GTT | CAT | ATT | ATT | 2854 |
| Asn | Gly | Leu | Tyr 900 | Gln | Val | Leu | Arg | Lys 905 | Asp | Lys | Asp | Val | His 910 | Ile | Ile | |
| CTC | GAT | AAA | CTC | AGC | AAT | GTA | ACG | GGA | TAT | GCC | TTT | TAT | CAG | CCA | GCA | 2902 |
| Leu | Asp | Lys 915 | Leu | Ser | Asn | Val | Thr 920 | Gly | Tyr | Ala | Phe | Tyr 925 | Gln | Pro | Ala | |
| TCA | ATT | GAA | GAC | AAA | TGG | ATC | AAA | AAG | GTT | AAT | AAA | CCT | GCA | ATT | GTG | 2950 |
| Ser | Ile 930 | Glu | Asp | Lys | Trp | Ile 935 | Lys | Lys | Val | Asn | Lys 940 | Pro | Ala | Ile | Val | |
| ATG | ACT | CAT | CGA | CAA | AAA | GAC | ACT | CTT | ATT | GTC | AGT | GCA | GTT | ACA | CCT | 2998 |
| Met 945 | Thr | His | Arg | Gln | AAA 950 | Asp | Thr | Leu | Ile | Val 955 | Ser | Ala | Val | Thr | Pro 960 | |
| GAT | TTA | AAT | ATG | ACT | CGC | CAA | AAA | GCA | GCA | ACT | CCT | GTC | ACC | ATC | AAT | 3046 |
| Asp | Leu | Asn | Met | Thr 965 | Arg | Gln | Lys | Ala | Ala 970 | Thr | Pro | Val | Thr | Ile 975 | Asn | |
| GTC | ACG | ATT | AAT | GGC | AAA | TGG | CAA | TCT | GCT | GAT | AAA | AAT | AGT | GAA | GTG | 3094 |
| Val | Thr | Ile | Asn 980 | Gly | Lys | Trp | Gln | Ser 985 | Ala | Asp | Lys | Asn | Ser 990 | Glu | Val | |
| AAA | TAT | CAG | GTT | TCT | GGT | GAT | AAC | ACT | GAA | CTG | ACG | TTT | ACG | AGT | TAC | 3142 |
| Lys | Tyr | Gln 995 | Val | Ser | Gly | Asp | Asn 1000 | Thr | Glu | Leu | Thr | Phe 1005 | Thr | Ser | Tyr | |
| TTT | GGT | ATT | CCA | CAA | GAA | ATC | AAA | CTC | TCG | CCA | CTC | CCT | TGATTTAATC | | | 3191 |
| Phe | Gly | Ile 1010 | Pro | Gln | Glu | Ile 1015 | Lys | Leu | Ser | Pro | Leu 1020 | Pro | | | | |

| | | | | |
|---|---|---|---|---|
| AAAGAACGC | TCTTGCGTTC | CTTTTTTATT | TGCAGGAAAT | CTGATTATGC | TAATAAAAAA | 3251 |
| CCCTTTAGCC | CACGCGGTTA | CATTAAGCCT | CTGTTTATCA | TTACCCGCAC | AAGCATTACC | 3311 |
| CACTCTGTCT | CATGAAGCTT | TCGGCGATAT | TTATCTTTTT | GAAGGTGAAT | TACCCAATAC | 3371 |
| CCTTACCACT | TCAAATAATA | ATCAATTATC | GCTAAGCAAA | CAGCATGCTA | AAGATGGTGA | 3431 |
| ACAATCACTC | AAATGGCAAT | ATCAACCACA | AGCAACATTA | ACACTAAATA | ATATTGTTAA | 3491 |
| TTACCAAGAT | GATAAAAATA | CAGCCACACC | ACTCACTTTT | ATGATGTGGA | TTTATAATGA | 3551 |
| AAAACCTCAA | TCTTCCCCAT | TAACGTTAGC | ATTTAAACAA | AATAATAAAA | TTGCACTAAG | 3611 |
| TTTTAATGCT | GAACTTAATT | TTACGGGGTG | GCGAGGTATT | GCTGTTCCTT | TTCGTGATAT | 3671 |
| GCAAGGCTCT | GCGACAGGTC | AACTTGATCA | ATTAGTGATC | ACCGCTCCAA | ACCAAGCCGG | 3731 |
| AACACTCTTT | TTTGATCAAA | TCATCATGAG | TGTACCGTTA | GACAATCGTT | GGGCAGTACC | 3791 |
| TGACTATCAA | ACACCTTACG | TAAATAACGC | AGTAAACACG | ATGGTTAGTA | AAAACTGGAG | 3851 |
| TGCATTATTG | ATGTACGATC | AGATGTTTCA | AGCCCATTAC | CCTACTTTAA | ACTTCGATAC | 3911 |
| TGAATTTCGC | GATGACCAAA | CAGAAATGGC | TTCGATTTAT | CAGCGCTTTG | AATATTATCA | 3971 |
| AGGAATTCC | | | | | | 3980 |

( 2 ) INFORMATION FOR SEQ ID NO:2:

( i ) SEQUENCE CHARACTERISTICS:
        ( A ) LENGTH: 1021 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Pro | Ile | Phe | Arg | Phe | Thr | Ala | Leu | Ala | Met | Thr | Leu | Gly | Leu | Leu |
| 1 | | | | 5 | | | | | 10 | | | | | 15 | |

-continued

| | | | | | | | | | | | | | |
|---|---|---|---|---|---|---|---|---|---|---|---|---|---|
| Ser | Ala | Pro | Tyr 20 | Asn | Ala | Met | Ala 25 | Thr | Ser | Asn | Pro 30 | Ala | Phe | Asp |
| Pro | Lys | Asn 35 | Leu | Met | Gln | Ser | Glu 40 | Ile | Tyr | His | Phe | Ala 45 | Gln | Asn | Asn |
| Pro | Leu | Ala 50 | Asp | Phe | Ser | Ser 55 | Asp | Lys | Asn | Ser | Ile 60 | Leu | Thr | Leu | Ser |
| Asp 65 | Lys | Arg | Ser | Ile | Met 70 | Gly | Asn | Gln | Ser | Leu 75 | Leu | Trp | Lys | Trp | Lys 80 |
| Gly | Gly | Ser | Ser | Phe 85 | Thr | Leu | His | Lys | Lys 90 | Leu | Ile | Val | Pro | Thr 95 | Asp |
| Lys | Glu | Ala | Ser 100 | Lys | Ala | Trp | Gly | Arg 105 | Ser | Ser | Thr | Pro | Val 110 | Phe | Ser |
| Phe | Trp | Leu 115 | Tyr | Asn | Glu | Lys | Pro 120 | Ile | Asp | Gly | Tyr | Leu 125 | Thr | Ile | Asp |
| Phe | Gly 130 | Glu | Lys | Leu | Ile | Ser 135 | Thr | Ser | Glu | Ala | Gln 140 | Ala | Gly | Phe | Lys |
| Val 145 | Lys | Leu | Asp | Phe | Thr 150 | Gly | Trp | Arg | Ala | Val 155 | Gly | Val | Ser | Leu | Asn 160 |
| Asn | Asp | Leu | Glu | Asn 165 | Arg | Glu | Met | Thr | Leu 170 | Asn | Ala | Thr | Asn | Thr 175 | Ser |
| Ser | Asp | Gly | Thr 180 | Gln | Asp | Ser | Ile | Gly 185 | Arg | Ser | Leu | Gly | Ala 190 | Lys | Val |
| Asp | Ser | Ile 195 | Arg | Phe | Lys | Ala | Pro 200 | Ser | Asn | Val | Ser | Gln 205 | Gly | Glu | Ile |
| Tyr | Ile 210 | Asp | Arg | Ile | Met | Phe 215 | Ser | Val | Asp | Asp | Ala 220 | Arg | Tyr | Gln | Trp |
| Ser 225 | Asp | Tyr | Gln | Val | Lys 230 | Thr | Arg | Leu | Ser | Glu 235 | Pro | Glu | Ile | Gln | Phe 240 |
| His | Asn | Val | Lys | Pro 245 | Gln | Leu | Pro | Val | Thr 250 | Pro | Glu | Asn | Leu | Ala 255 | Ala |
| Ile | Asp | Leu | Ile 260 | Arg | Gln | Arg | Leu | Ile 265 | Asn | Glu | Phe | Val | Gly 270 | Gly | Glu |
| Lys | Glu | Thr 275 | Asn | Leu | Ala | Leu | Glu 280 | Glu | Asn | Ile | Ser | Lys 285 | Leu | Lys | Ser |
| Asp | Phe 290 | Asp | Ala | Leu | Asn | Ile 295 | His | Thr | Leu | Ala | Asn 300 | Gly | Gly | Thr | Gln |
| Gly 305 | Arg | His | Leu | Ile | Thr 310 | Asp | Lys | Gln | Ile | Ile 315 | Ile | Tyr | Gln | Pro | Glu 320 |
| Asn | Leu | Asn | Ser | Gln 325 | Asp | Lys | Gln | Leu | Phe 330 | Asp | Asn | Tyr | Val | Ile 335 | Leu |
| Gly | Asn | Tyr | Thr 340 | Thr | Leu | Met | Phe | Asn 345 | Ile | Ser | Arg | Ala | Tyr 350 | Val | Leu |
| Glu | Lys | Asp 355 | Pro | Thr | Gln | Lys | Ala 360 | Gln | Leu | Lys | Gln | Met 365 | Tyr | Leu | Leu |
| Met | Thr 370 | Lys | His | Leu | Leu | Asp 375 | Gln | Gly | Phe | Val | Lys 380 | Gly | Ser | Ala | Leu |
| Val 385 | Thr | Thr | His | His | Trp 390 | Gly | Tyr | Ser | Ser | Arg 395 | Trp | Trp | Tyr | Ile | Ser 400 |
| Thr | Leu | Leu | Met | Ser 405 | Asp | Ala | Leu | Lys | Glu 410 | Ala | Asn | Leu | Gln | Thr 415 | Gln |
| Val | Tyr | Asp | Ser 420 | Leu | Leu | Trp | Tyr | Ser 425 | Arg | Glu | Phe | Lys | Ser 430 | Ser | Phe |
| Asp | Met | Lys | Val | Ser | Ala | Asp | Ser | Ser | Asp | Leu | Asp | Tyr | Phe | Asn | Thr |

```
                      435                           440                            445
Leu  Ser  Arg  Gln  His  Leu  Ala  Leu  Leu  Leu  Leu  Glu  Pro  Asp  Asp  Gln
          450                      455                      460

Lys  Arg  Ile  Asn  Leu  Val  Asn  Thr  Phe  Ser  His  Tyr  Ile  Thr  Gly  Ala
465                      470                      475                           480

Leu  Thr  Gln  Val  Pro  Pro  Gly  Gly  Lys  Asp  Gly  Leu  Arg  Pro  Asp  Gly
                    485                      490                     495

Thr  Ala  Trp  Arg  His  Glu  Gly  Asn  Tyr  Pro  Gly  Tyr  Ser  Phe  Pro  Ala
                    500                      505                     510

Phe  Lys  Asn  Ala  Ser  Gln  Leu  Ile  Tyr  Leu  Leu  Arg  Asp  Thr  Pro  Phe
          515                      520                     525

Ser  Val  Gly  Glu  Ser  Gly  Trp  Asn  Asn  Leu  Lys  Lys  Ala  Met  Val  Ser
     530                      535                     540

Ala  Trp  Ile  Tyr  Ser  Asn  Pro  Glu  Val  Gly  Leu  Pro  Leu  Ala  Gly  Arg
545                      550                     555                          560

His  Pro  Phe  Asn  Ser  Pro  Ser  Leu  Lys  Ser  Val  Ala  Gln  Gly  Tyr  Tyr
                    565                     570                     575

Trp  Leu  Ala  Met  Ser  Ala  Lys  Ser  Ser  Pro  Asp  Lys  Thr  Leu  Ala  Ser
               580                     585                     590

Ile  Tyr  Leu  Ala  Ile  Ser  Asp  Lys  Thr  Gln  Asn  Glu  Ser  Thr  Ala  Ile
          595                     600                     605

Phe  Gly  Glu  Thr  Ile  Thr  Pro  Ala  Ser  Leu  Pro  Gln  Gly  Phe  Tyr  Ala
     610                     615                     620

Phe  Asn  Gly  Gly  Ala  Phe  Gly  Ile  His  Arg  Trp  Gln  Asp  Lys  Met  Val
625                     630                     635                          640

Thr  Leu  Lys  Ala  Tyr  Asn  Thr  Asn  Val  Trp  Ser  Ser  Glu  Ile  Tyr  Asn
                    645                     650                     655

Lys  Asp  Asn  Arg  Tyr  Gly  Arg  Tyr  Gln  Ser  His  Gly  Val  Ala  Gln  Ile
               660                     665                     670

Val  Ser  Asn  Gly  Ser  Gln  Leu  Ser  Gln  Gly  Tyr  Gln  Gln  Glu  Gly  Trp
          675                     680                     685

Asp  Trp  Asn  Arg  Met  Gln  Gly  Ala  Thr  Thr  Ile  His  Leu  Pro  Leu  Lys
     690                     695                     700

Asp  Leu  Asp  Ser  Pro  Lys  Pro  His  Thr  Leu  Met  Gln  Arg  Gly  Glu  Arg
705                     710                     715                          720

Gly  Phe  Ser  Gly  Thr  Ser  Ser  Leu  Glu  Gly  Gln  Tyr  Gly  Met  Met  Ala
                    725                     730                     735

Phe  Asp  Leu  Ile  Tyr  Pro  Ala  Asn  Leu  Glu  Arg  Phe  Asp  Pro  Asn  Phe
               740                     745                     750

Thr  Ala  Lys  Lys  Ser  Val  Leu  Ala  Ala  Asp  Asn  His  Leu  Ile  Phe  Ile
          755                     760                     765

Gly  Ser  Asn  Ile  Asn  Ser  Ser  Asp  Lys  Asn  Lys  Asn  Val  Glu  Thr  Thr
     770                     775                     780

Leu  Phe  Gln  His  Ala  Ile  Thr  Pro  Thr  Leu  Asn  Thr  Leu  Trp  Ile  Asn
785                     790                     795                          800

Gly  Gln  Lys  Ile  Glu  Asn  Met  Pro  Tyr  Gln  Thr  Thr  Leu  Gln  Gln  Gly
                    805                     810                     815

Asp  Trp  Leu  Ile  Asp  Ser  Asn  Gly  Asn  Gly  Tyr  Leu  Ile  Thr  Gln  Ala
               820                     825                     830

Glu  Lys  Val  Asn  Val  Ser  Arg  Gln  His  Gln  Val  Ser  Ala  Glu  Asn  Lys
          835                     840                     845

Asn  Arg  Gln  Pro  Thr  Glu  Gly  Asn  Phe  Ser  Ser  Ala  Trp  Ile  Asp  His
     850                     855                     860
```

| Ser | Thr | Arg | Pro | Lys | Asp | Ala | Ser | Tyr | Glu | Tyr | Met | Val | Phe | Leu | Asp |
| 865 | | | | 870 | | | | 875 | | | | | | | 880 |

| Ala | Thr | Pro | Glu | Lys | Met | Gly | Glu | Met | Ala | Gln | Lys | Phe | Arg | Glu | Asn |
| | | | | 885 | | | | | 890 | | | | | 895 | |

| Asn | Gly | Leu | Tyr | Gln | Val | Leu | Arg | Lys | Asp | Lys | Asp | Val | His | Ile | Ile |
| | | | 900 | | | | | 905 | | | | | 910 | | |

| Leu | Asp | Lys | Leu | Ser | Asn | Val | Thr | Gly | Tyr | Ala | Phe | Tyr | Gln | Pro | Ala |
| | | 915 | | | | | 920 | | | | | 925 | | | |

| Ser | Ile | Glu | Asp | Lys | Trp | Ile | Lys | Lys | Val | Asn | Lys | Pro | Ala | Ile | Val |
| | 930 | | | | | 935 | | | | | 940 | | | | |

| Met | Thr | His | Arg | Gln | Lys | Asp | Thr | Leu | Ile | Val | Ser | Ala | Val | Thr | Pro |
| 945 | | | | | 950 | | | | | 955 | | | | | 960 |

| Asp | Leu | Asn | Met | Thr | Arg | Gln | Lys | Ala | Ala | Thr | Pro | Val | Thr | Ile | Asn |
| | | | | 965 | | | | | 970 | | | | | 975 | |

| Val | Thr | Ile | Asn | Gly | Lys | Trp | Gln | Ser | Ala | Asp | Lys | Asn | Ser | Glu | Val |
| | | | 980 | | | | | 985 | | | | | 990 | | |

| Lys | Tyr | Gln | Val | Ser | Gly | Asp | Asn | Thr | Glu | Leu | Thr | Phe | Thr | Ser | Tyr |
| | | 995 | | | | | 1000 | | | | | 1005 | | | |

| Phe | Gly | Ile | Pro | Gln | Glu | Ile | Lys | Leu | Ser | Pro | Leu | Pro |
| | | | | 1010 | | | 1015 | | | | 1020 | |

( 2 ) INFORMATION FOR SEQ ID NO:3:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

GCCAGCGTTT CTAAGGAGAA AACATATGCC GATATTTCGT TTTACTGC      48

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

GCGCCTTATA ACGCGCATAT GGCCACCAGC AATCCTG      37

( 2 ) INFORMATION FOR SEQ ID NO:5:

( i ) SEQUENCE CHARACTERISTICS:
        ( A ) LENGTH: 3980 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: CDS
    ( B ) LOCATION: 188..3181

( x i ) SEQUENCE DESCRIPTION: SEQ ID NO:5:

```
GGAATTCCAT CACTCAATCA TTAAATTTAG GCACAACGAT GGGCTATCAG CGTTATGACA          60

AATTTAATGA AGGACGCATT GGTTTCACTG TTAGCCAGCG TTTCTAAGGA GAAAAATAAT         120

GCCGATATTT CGTTTTACTG CACTTGCAAT GACATTGGGG CTATTATCAG CGCCTTATAA         180

CGCGGAT ATG GCC ACC AGC AAT CCT GCA TTT GAT CCT AAA AAT CTG ATG           229
        Met Ala Thr Ser Asn Pro Ala Phe Asp Pro Lys Asn Leu Met
         1               5                  10

CAG TCA GAA ATT TAC CAT TTT GCA CAA AAT AAC CCA TTA GCA GAC TTC           277
Gln Ser Glu Ile Tyr His Phe Ala Gln Asn Asn Pro Leu Ala Asp Phe
 15              20                  25                  30

TCA TCA GAT AAA AAC TCA ATA CTA ACG TTA TCT GAT AAA CGT AGC ATT           325
Ser Ser Asp Lys Asn Ser Ile Leu Thr Leu Ser Asp Lys Arg Ser Ile
                 35                  40                  45

ATG GGA AAC CAA TCT CTT TTA TGG AAA TGG AAA GGT GGT AGT AGC TTT           373
Met Gly Asn Gln Ser Leu Leu Trp Lys Trp Lys Gly Gly Ser Ser Phe
             50                  55                  60

ACT TTA CAT AAA AAA CTG ATT GTC CCC ACC GAT AAA GAA GCA TCT AAA           421
Thr Leu His Lys Lys Leu Ile Val Pro Thr Asp Lys Glu Ala Ser Lys
         65                  70                  75

GCA TGG GGA CGC TCA TCT ACC CCC GTT TTC TCA TTT TGG CTT TAC AAT           469
Ala Trp Gly Arg Ser Ser Thr Pro Val Phe Ser Phe Trp Leu Tyr Asn
     80                  85                  90

GAA AAA CCG ATT GAT GGT TAT CTT ACT ATC GAT TTC GGA GAA AAA CTC           517
Glu Lys Pro Ile Asp Gly Tyr Leu Thr Ile Asp Phe Gly Glu Lys Leu
 95                 100                 105                 110

ATT TCA ACC AGT GAG GCT CAG GCA GGC TTT AAA GTA AAA TTA GAT TTC           565
Ile Ser Thr Ser Glu Ala Gln Ala Gly Phe Lys Val Lys Leu Asp Phe
                115                 120                 125

ACT GGC TGG CGT GCT GTG GGA GTC TCT TTA AAT AAC GAT CTT GAA AAT           613
Thr Gly Trp Arg Ala Val Gly Val Ser Leu Asn Asn Asp Leu Glu Asn
            130                 135                 140

CGA GAG ATG ACC TTA AAT GCA ACC AAT ACC TCC TCT GAT GGT ACT CAA           661
Arg Glu Met Thr Leu Asn Ala Thr Asn Thr Ser Ser Asp Gly Thr Gln
        145                 150                 155

GAC AGC ATT GGG CGT TCT TTA GGT GCT AAA GTC GAT AGT ATT CGT TTT           709
Asp Ser Ile Gly Arg Ser Leu Gly Ala Lys Val Asp Ser Ile Arg Phe
160                 165                 170

AAA GCG CCT TCT AAT GTG AGT CAG GGT GAA ATC TAT ATC GAC CGT ATT           757
Lys Ala Pro Ser Asn Val Ser Gln Gly Glu Ile Tyr Ile Asp Arg Ile
175                 180                 185                 190

ATG TTT TCT GTC GAT GAT GCT CGC TAC CAA TGG TCT GAT TAT CAA GTA           805
Met Phe Ser Val Asp Asp Ala Arg Tyr Gln Trp Ser Asp Tyr Gln Val
                195                 200                 205

AAA ACT CGC TTA TCA GAA CCT GAA ATT CAA TTT CAC AAC GTA AAG CCA           853
Lys Thr Arg Leu Ser Glu Pro Glu Ile Gln Phe His Asn Val Lys Pro
            210                 215                 220

CAA CTA CCT GTA ACA CCT GAA AAT TTA GCG GCC ATT GAT CTT ATT CGC           901
Gln Leu Pro Val Thr Pro Glu Asn Leu Ala Ala Ile Asp Leu Ile Arg
        225                 230                 235

CAA CGT CTA ATT AAT GAA TTT GTC GGA GGT GAA AAA GAG ACA AAC CTC           949
Gln Arg Leu Ile Asn Glu Phe Val Gly Gly Glu Lys Glu Thr Asn Leu
240                 245                 250

GCA TTA GAA GAG AAT ATC AGC AAA TTA AAA AGT GAT TTC GAT GCT CTT           997
```

-continued

| | | | | | | | | | | | | | | | |
|---|---|---|---|---|---|---|---|---|---|---|---|---|---|---|---|
| Ala | Leu | Glu | Glu | Asn | Ile | Ser | Lys | Leu | Lys | Ser | Asp | Phe | Asp | Ala | Leu |
| 255 | | | | 260 | | | | | 265 | | | | | 270 | |

| AAT | ATT | CAC | ACT | TTA | GCA | AAT | GGT | GGA | ACG | CAA | GGC | AGA | CAT | CTG | ATC | 1045 |
|---|---|---|---|---|---|---|---|---|---|---|---|---|---|---|---|---|
| Asn | Ile | His | Thr | Leu | Ala | Asn | Gly | Gly | Thr | Gln | Gly | Arg | His | Leu | Ile | |
| | | | | 275 | | | | 280 | | | | | 285 | | | |

| ACT | GAT | AAA | CAA | ATC | ATT | ATT | TAT | CAA | CCA | GAG | AAT | CTT | AAC | TCC | CAA | 1093 |
|---|---|---|---|---|---|---|---|---|---|---|---|---|---|---|---|---|
| Thr | Asp | Lys | Gln | Ile | Ile | Ile | Tyr | Gln | Pro | Glu | Asn | Leu | Asn | Ser | Gln | |
| | | | 290 | | | | | 295 | | | | | 300 | | | |

| GAT | AAA | CAA | CTA | TTT | GAT | AAT | TAT | GTT | ATT | TTA | GGT | AAT | TAC | ACG | ACA | 1141 |
|---|---|---|---|---|---|---|---|---|---|---|---|---|---|---|---|---|
| Asp | Lys | Gln | Leu | Phe | Asp | Asn | Tyr | Val | Ile | Leu | Gly | Asn | Tyr | Thr | Thr | |
| | | | 305 | | | | 310 | | | | | 315 | | | | |

| TTA | ATG | TTT | AAT | ATT | AGC | CGT | GCT | TAT | GTG | CTG | GAA | AAA | GAT | CCC | ACA | 1189 |
|---|---|---|---|---|---|---|---|---|---|---|---|---|---|---|---|---|
| Leu | Met | Phe | Asn | Ile | Ser | Arg | Ala | Tyr | Val | Leu | Glu | Lys | Asp | Pro | Thr | |
| | | 320 | | | | 325 | | | | | 330 | | | | | |

| CAA | AAG | GCG | CAA | CTA | AAG | CAG | ATG | TAC | TTA | TTA | ATG | ACA | AAG | CAT | TTA | 1237 |
|---|---|---|---|---|---|---|---|---|---|---|---|---|---|---|---|---|
| Gln | Lys | Ala | Gln | Leu | Lys | Gln | Met | Tyr | Leu | Leu | Met | Thr | Lys | His | Leu | |
| 335 | | | | | 340 | | | | | 345 | | | | | 350 | |

| TTA | GAT | CAA | GGC | TTT | GTT | AAA | GGG | AGT | GCT | TTA | GTG | ACA | ACC | CAT | CAC | 1285 |
|---|---|---|---|---|---|---|---|---|---|---|---|---|---|---|---|---|
| Leu | Asp | Gln | Gly | Phe | Val | Lys | Gly | Ser | Ala | Leu | Val | Thr | Thr | His | His | |
| | | | | 355 | | | | | 360 | | | | | 365 | | |

| TGG | GGA | TAC | AGT | TCT | CGT | TGG | TGG | TAT | ATT | TCC | ACG | TTA | TTA | ATG | TCT | 1333 |
|---|---|---|---|---|---|---|---|---|---|---|---|---|---|---|---|---|
| Trp | Gly | Tyr | Ser | Ser | Arg | Trp | Trp | Tyr | Ile | Ser | Thr | Leu | Leu | Met | Ser | |
| | | | 370 | | | | | 375 | | | | | 380 | | | |

| GAT | GCA | CTA | AAA | GAA | GCG | AAC | CTA | CAA | ACT | CAA | GTT | TAT | GAT | TCA | TTA | 1381 |
|---|---|---|---|---|---|---|---|---|---|---|---|---|---|---|---|---|
| Asp | Ala | Leu | Lys | Glu | Ala | Asn | Leu | Gln | Thr | Gln | Val | Tyr | Asp | Ser | Leu | |
| | | 385 | | | | | 390 | | | | | 395 | | | | |

| CTG | TGG | TAT | TCA | CGT | GAG | TTT | AAA | AGT | AGT | TTT | GAT | ATG | AAA | GTA | AGT | 1429 |
|---|---|---|---|---|---|---|---|---|---|---|---|---|---|---|---|---|
| Leu | Trp | Tyr | Ser | Arg | Glu | Phe | Lys | Ser | Ser | Phe | Asp | Met | Lys | Val | Ser | |
| | 400 | | | | | 405 | | | | | 410 | | | | | |

| GCT | GAT | AGC | TCT | GAT | CTA | GAT | TAT | TTC | AAT | ACC | TTA | TCT | CGC | CAA | CAT | 1477 |
|---|---|---|---|---|---|---|---|---|---|---|---|---|---|---|---|---|
| Ala | Asp | Ser | Ser | Asp | Leu | Asp | Tyr | Phe | Asn | Thr | Leu | Ser | Arg | Gln | His | |
| 415 | | | | | 420 | | | | | 425 | | | | | 430 | |

| TTA | GCC | TTA | TTA | TTA | CTA | GAG | CCT | GAT | GAT | CAA | AAG | CGT | ATC | AAC | TTA | 1525 |
|---|---|---|---|---|---|---|---|---|---|---|---|---|---|---|---|---|
| Leu | Ala | Leu | Leu | Leu | Leu | Glu | Pro | Asp | Asp | Gln | Lys | Arg | Ile | Asn | Leu | |
| | | | | 435 | | | | | 440 | | | | | 445 | | |

| GTT | AAT | ACT | TTC | AGC | CAT | TAT | ATC | ACT | GGC | GCA | TTA | ACG | CAA | GTG | CCA | 1573 |
|---|---|---|---|---|---|---|---|---|---|---|---|---|---|---|---|---|
| Val | Asn | Thr | Phe | Ser | His | Tyr | Ile | Thr | Gly | Ala | Leu | Thr | Gln | Val | Pro | |
| | | | 450 | | | | | 455 | | | | | 460 | | | |

| CCG | GGT | GGT | AAA | GAT | GGT | TTA | CGC | CCT | GAT | GGT | ACA | GCA | TGG | CGA | CAT | 1621 |
|---|---|---|---|---|---|---|---|---|---|---|---|---|---|---|---|---|
| Pro | Gly | Gly | Lys | Asp | Gly | Leu | Arg | Pro | Asp | Gly | Thr | Ala | Trp | Arg | His | |
| | | 465 | | | | | 470 | | | | | 475 | | | | |

| GAA | GGC | AAC | TAT | CCG | GGC | TAC | TCT | TTC | CCA | GCC | TTT | AAA | AAT | GCC | TCT | 1669 |
|---|---|---|---|---|---|---|---|---|---|---|---|---|---|---|---|---|
| Glu | Gly | Asn | Tyr | Pro | Gly | Tyr | Ser | Phe | Pro | Ala | Phe | Lys | Asn | Ala | Ser | |
| | | 480 | | | | | 485 | | | | | 490 | | | | |

| CAG | CTT | ATT | TAT | TTA | TTA | CGC | GAT | ACA | CCA | TTT | TCA | GTG | GGT | GAA | AGT | 1717 |
|---|---|---|---|---|---|---|---|---|---|---|---|---|---|---|---|---|
| Gln | Leu | Ile | Tyr | Leu | Leu | Arg | Asp | Thr | Pro | Phe | Ser | Val | Gly | Glu | Ser | |
| 495 | | | | | 500 | | | | | 505 | | | | | 510 | |

| GGT | TGG | AAT | AAC | CTG | AAA | AAA | GCG | ATG | GTT | TCA | GCG | TGG | ATC | TAC | AGT | 1765 |
|---|---|---|---|---|---|---|---|---|---|---|---|---|---|---|---|---|
| Gly | Trp | Asn | Asn | Leu | Lys | Lys | Ala | Met | Val | Ser | Ala | Trp | Ile | Tyr | Ser | |
| | | | | 515 | | | | | 520 | | | | | 525 | | |

| AAT | CCA | GAA | GTT | GGA | TTA | CCG | CTT | GCA | GGA | AGA | CAC | CCT | TTT | AAC | TCA | 1813 |
|---|---|---|---|---|---|---|---|---|---|---|---|---|---|---|---|---|
| Asn | Pro | Glu | Val | Gly | Leu | Pro | Leu | Ala | Gly | Arg | His | Pro | Phe | Asn | Ser | |
| | | | 530 | | | | 535 | | | | | 540 | | | | |

| CCT | TCG | TTA | AAA | TCA | GTC | GCT | CAA | GGC | TAT | TAC | TGG | CTT | GCC | ATG | TCT | 1861 |
|---|---|---|---|---|---|---|---|---|---|---|---|---|---|---|---|---|
| Pro | Ser | Leu | Lys | Ser | Val | Ala | Gln | Gly | Tyr | Tyr | Trp | Leu | Ala | Met | Ser | |
| | | | 545 | | | | | 550 | | | | | 555 | | | |

| GCA | AAA | TCA | TCG | CCT | GAT | AAA | ACA | CTT | GCA | TCT | ATT | TAT | CTT | GCG | ATT | 1909 |
|---|---|---|---|---|---|---|---|---|---|---|---|---|---|---|---|---|
| Ala | Lys | Ser | Ser | Pro | Asp | Lys | Thr | Leu | Ala | Ser | Ile | Tyr | Leu | Ala | Ile | |
| | 560 | | | | | 565 | | | | | 570 | | | | | |

| AGT | GAT | AAA | ACA | CAA | AAT | GAA | TCA | ACT | GCT | ATT | TTT | GGA | GAA | ACT | ATT | 1957 |

| | | | | | | | | | | | | | | | | |
|---|---|---|---|---|---|---|---|---|---|---|---|---|---|---|---|---|
| Ser<br>575 | Asp | Lys | Thr | Gln | Asn<br>580 | Glu | Ser | Thr | Ala | Ile<br>585 | Phe | Gly | Glu | Thr | Ile<br>590 | |

| ACA | CCA | GCG | TCT | TTA | CCT | CAA | GGT | TTC | TAT | GCC | TTT | AAT | GGC | GGT | GCT | 2005 |
|---|---|---|---|---|---|---|---|---|---|---|---|---|---|---|---|---|
| Thr | Pro | Ala | Ser | Leu<br>595 | Pro | Gln | Gly | Phe | Tyr<br>600 | Ala | Phe | Asn | Gly | Gly<br>605 | Ala | |

| TTT | GGT | ATT | CAT | CGT | TGG | CAA | GAT | AAA | ATG | GTG | ACA | CTG | AAA | GCT | TAT | 2053 |
|---|---|---|---|---|---|---|---|---|---|---|---|---|---|---|---|---|
| Phe | Gly | Ile | His<br>610 | Arg | Trp | Gln | Asp | Lys<br>615 | Met | Val | Thr | Leu | Lys<br>620 | Ala | Tyr | |

| AAC | ACC | AAT | GTT | TGG | TCA | TCT | GAA | ATT | TAT | AAC | AAA | GAT | AAC | CGT | TAT | 2101 |
|---|---|---|---|---|---|---|---|---|---|---|---|---|---|---|---|---|
| Asn | Thr | Asn<br>625 | Val | Trp | Ser | Ser | Glu<br>630 | Ile | Tyr | Asn | Lys | Asp<br>635 | Asn | Arg | Tyr | |

| GGC | CGT | TAC | CAA | AGT | CAT | GGT | GTC | GCT | CAA | ATA | GTG | AGT | AAT | GGC | TCG | 2149 |
|---|---|---|---|---|---|---|---|---|---|---|---|---|---|---|---|---|
| Gly | Arg<br>640 | Tyr | Gln | Ser | His<br>645 | Gly | Val | Ala | Gln | Ile<br>650 | Val | Ser | Asn | Gly | Ser | |

| CAG | CTT | TCA | CAG | GGC | TAT | CAG | CAA | GAA | GGT | TGG | GAT | TGG | AAT | AGA | ATG | 2197 |
|---|---|---|---|---|---|---|---|---|---|---|---|---|---|---|---|---|
| Gln<br>655 | Leu | Ser | Gln | Gly | Tyr<br>660 | Gln | Gln | Glu | Gly | Trp<br>665 | Asp | Trp | Asn | Arg | Met<br>670 | |

| CAA | GGG | GCA | ACC | ACT | ATT | CAC | CTT | CCT | CTT | AAA | GAC | TTA | GAC | AGT | CCT | 2245 |
|---|---|---|---|---|---|---|---|---|---|---|---|---|---|---|---|---|
| Gln | Gly | Ala | Thr | Thr<br>675 | Ile | His | Leu | Pro | Leu<br>680 | Lys | Asp | Leu | Asp | Ser<br>685 | Pro | |

| AAA | CCT | CAT | ACC | TTA | ATG | CAA | CGT | GGA | GAG | CGT | GGA | TTT | AGC | GGA | ACA | 2293 |
|---|---|---|---|---|---|---|---|---|---|---|---|---|---|---|---|---|
| Lys | Pro | His | Thr<br>690 | Leu | Met | Gln | Arg | Gly<br>695 | Glu | Arg | Gly | Phe | Ser<br>700 | Gly | Thr | |

| TCA | TCC | CTT | GAA | GGT | CAA | TAT | GGC | ATG | ATG | GCA | TTC | GAT | CTT | ATT | TAT | 2341 |
|---|---|---|---|---|---|---|---|---|---|---|---|---|---|---|---|---|
| Ser | Ser | Leu<br>705 | Glu | Gly | Gln | Tyr | Gly<br>710 | Met | Met | Ala | Phe | Asp<br>715 | Leu | Ile | Tyr | |

| CCC | GCC | AAT | CTT | GAG | CGT | TTT | GAT | CCT | AAT | TTC | ACT | GCG | AAA | AAG | AGT | 2389 |
|---|---|---|---|---|---|---|---|---|---|---|---|---|---|---|---|---|
| Pro | Ala | Asn<br>720 | Leu | Glu | Arg | Phe<br>725 | Asp | Pro | Asn | Phe | Thr<br>730 | Ala | Lys | Lys | Ser | |

| GTA | TTA | GCC | GCT | GAT | AAT | CAC | TTA | ATT | TTT | ATT | GGT | AGC | AAT | ATA | AAT | 2437 |
|---|---|---|---|---|---|---|---|---|---|---|---|---|---|---|---|---|
| Val<br>735 | Leu | Ala | Ala | Asp | Asn<br>740 | His | Leu | Ile | Phe | Ile<br>745 | Gly | Ser | Asn | Ile | Asn<br>750 | |

| AGT | AGT | GAT | AAA | AAT | AAA | AAT | GTT | GAA | ACG | ACC | TTA | TTC | CAA | CAT | GCC | 2485 |
|---|---|---|---|---|---|---|---|---|---|---|---|---|---|---|---|---|
| Ser | Ser | Asp | Lys | Asn<br>755 | Lys | Asn | Val | Glu | Thr<br>760 | Thr | Leu | Phe | Gln | His<br>765 | Ala | |

| ATT | ACT | CCA | ACA | TTA | AAT | ACC | CTT | TGG | ATT | AAT | GGA | CAA | AAG | ATA | GAA | 2533 |
|---|---|---|---|---|---|---|---|---|---|---|---|---|---|---|---|---|
| Ile | Thr | Pro | Thr<br>770 | Leu | Asn | Thr | Leu | Trp<br>775 | Ile | Asn | Gly | Gln | Lys<br>780 | Ile | Glu | |

| AAC | ATG | CCT | TAT | CAA | ACA | ACA | CTT | CAA | CAA | GGT | GAT | TGG | TTA | ATT | GAT | 2581 |
|---|---|---|---|---|---|---|---|---|---|---|---|---|---|---|---|---|
| Asn | Met | Pro<br>785 | Tyr | Gln | Thr | Thr | Leu<br>790 | Gln | Gln | Gly | Asp | Trp<br>795 | Leu | Ile | Asp | |

| AGC | AAT | GGC | AAT | GGT | TAC | TTA | ATT | ACT | CAA | GCA | GAA | AAA | GTA | AAT | GTA | 2629 |
|---|---|---|---|---|---|---|---|---|---|---|---|---|---|---|---|---|
| Ser | Asn | Gly<br>800 | Asn | Gly | Tyr | Leu | Ile<br>805 | Thr | Gln | Ala | Glu | Lys<br>810 | Val | Asn | Val | |

| AGT | CGC | CAA | CAT | CAG | GTT | TCA | GCG | GAA | AAT | AAA | AAT | CGC | CAA | CCG | ACA | 2677 |
|---|---|---|---|---|---|---|---|---|---|---|---|---|---|---|---|---|
| Ser | Arg<br>815 | Gln | His | Gln | Val<br>820 | Ser | Ala | Glu | Asn | Lys<br>825 | Asn | Arg | Gln | Pro | Thr<br>830 | |

| GAA | GGA | AAC | TTT | AGC | TCG | GCA | TGG | ATC | GAT | CAC | AGC | ACT | CGC | CCC | AAA | 2725 |
|---|---|---|---|---|---|---|---|---|---|---|---|---|---|---|---|---|
| Glu | Gly | Asn | Phe | Ser<br>835 | Ser | Ala | Trp | Ile | Asp<br>840 | His | Ser | Thr | Arg | Pro<br>845 | Lys | |

| GAT | GCC | AGT | TAT | GAG | TAT | ATG | GTC | TTT | TTA | GAT | GCG | ACA | CCT | GAA | AAA | 2773 |
|---|---|---|---|---|---|---|---|---|---|---|---|---|---|---|---|---|
| Asp | Ala | Ser | Tyr<br>850 | Glu | Tyr | Met | Val | Phe<br>855 | Leu | Asp | Ala | Thr | Pro<br>860 | Glu | Lys | |

| ATG | GGA | GAG | ATG | GCA | CAA | AAA | TTC | CGT | GAA | AAT | AAT | GGG | TTA | TAT | CAG | 2821 |
|---|---|---|---|---|---|---|---|---|---|---|---|---|---|---|---|---|
| Met | Gly | Glu<br>865 | Met | Ala | Gln | Lys | Phe<br>870 | Arg | Glu | Asn | Asn | Gly<br>875 | Leu | Tyr | Gln | |

| GTT | CTT | CGT | AAG | GAT | AAA | GAC | GTT | CAT | ATT | ATT | CTC | GAT | AAA | CTC | AGC | 2869 |
|---|---|---|---|---|---|---|---|---|---|---|---|---|---|---|---|---|
| Val | Leu | Arg<br>880 | Lys | Asp | Lys | Asp | Val<br>885 | His | Ile | Ile | Leu | Asp<br>890 | Lys | Leu | Ser | |

| AAT | GTA | ACG | GGA | TAT | GCC | TTT | TAT | CAG | CCA | GCA | TCA | ATT | GAA | GAC | AAA | 2917 |
|---|---|---|---|---|---|---|---|---|---|---|---|---|---|---|---|---|

-continued

| | | | | | | | | | | | | | | |
|---|---|---|---|---|---|---|---|---|---|---|---|---|---|---|
| Asn | Val | Thr | Gly | Tyr | Ala | Phe | Tyr | Gln | Pro | Ala | Ser | Ile | Glu | Asp | Lys |
| 895 | | | | 900 | | | | | 905 | | | | | 910 | |

```
TGG ATC AAA AAG GTT AAT AAA CCT GCA ATT GTG ATG ACT CAT CGA CAA    2965
Trp Ile Lys Lys Val Asn Lys Pro Ala Ile Val Met Thr His Arg Gln
            915                 920                 925

AAA GAC ACT CTT ATT GTC AGT GCA GTT ACA CCT GAT TTA AAT ATG ACT    3013
Lys Asp Thr Leu Ile Val Ser Ala Val Thr Pro Asp Leu Asn Met Thr
            930                 935                 940

CGC CAA AAA GCA GCA ACT CCT GTC ACC ATC AAT GTC ACG ATT AAT GGC    3061
Arg Gln Lys Ala Ala Thr Pro Val Thr Ile Asn Val Thr Ile Asn Gly
            945                 950                 955

AAA TGG CAA TCT GCT GAT AAA AAT AGT GAA GTG AAA TAT CAG GTT TCT    3109
Lys Trp Gln Ser Ala Asp Lys Asn Ser Glu Val Lys Tyr Gln Val Ser
            960                 965                 970

GGT GAT AAC ACT GAA CTG ACG TTT ACG AGT TAC TTT GGT ATT CCA CAA    3157
Gly Asp Asn Thr Glu Leu Thr Phe Thr Ser Tyr Phe Gly Ile Pro Gln
975             980                 985                 990

GAA ATC AAA CTC TCG CCA CTC CCT TGATTTAATC AAAAGAACGC TCTTGCGTTC    3211
Glu Ile Lys Leu Ser Pro Leu Pro
            995

CTTTTTTATT TGCAGGAAAT CTGATTATGC TAATAAAAAA CCCTTTAGCC CACGCGGTTA    3271
CATTAAGCCT CTGTTTATCA TTACCCGCAC AAGCATTACC CACTCTGTCT CATGAAGCTT    3331
TCGGCGATAT TTATCTTTTT GAAGGTGAAT TACCCAATAC CCTTACCACT TCAAATAATA    3391
ATCAATTATC GCTAAGCAAA CAGCATGCTA AGATGGTGA ACAATCACTC AAATGGCAAT    3451
ATCAACCACA AGCAACATTA ACACTAAATA ATATTGTTAA TTACCAAGAT GATAAAAATA    3511
CAGCCACACC ACTCACTTTT ATGATGTGGA TTTATAATGA AAAACCTCAA TCTTCCCCAT    3571
TAACGTTAGC ATTTAAACAA AATAATAAAA TTGCACTAAG TTTTAATGCT GAACTTAATT    3631
TTACGGGGTG GCGAGGTATT GCTGTTCCTT TCGTGATAT GCAAGGCTCT GCGACAGGTC    3691
AACTTGATCA ATTAGTGATC ACCGCTCCAA ACCAAGCCGG AACACTCTTT TTTGATCAAA    3751
TCATCATGAG TGTACCGTTA GACAATCGTT GGGCAGTACC TGACTATCAA ACACCTTACG    3811
TAAATAACGC AGTAAACACG ATGGTTAGTA AAAACTGGAG TGCATTATTG ATGTACGATC    3871
AGATGTTTCA AGCCCATTAC CCTACTTTAA ACTTCGATAC TGAATTTCGC GATGACCAAA    3931
CAGAAATGGC TTCGATTTAT CAGCGCTTTG AATATTATCA AGGAATTCC            3980
```

( 2 ) INFORMATION FOR SEQ ID NO:6:

( i ) SEQUENCE CHARACTERISTICS:
        ( A ) LENGTH: 998 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|---|
| Met | Ala | Thr | Ser | Asn | Pro | Ala | Phe | Asp | Pro | Lys | Asn | Leu | Met | Gln | Ser |
| 1 | | | | 5 | | | | | 10 | | | | | 15 | |
| Glu | Ile | Tyr | His | Phe | Ala | Gln | Asn | Asn | Pro | Leu | Ala | Asp | Phe | Ser | Ser |
| | | | 20 | | | | | 25 | | | | | 30 | | |
| Asp | Lys | Asn | Ser | Ile | Leu | Thr | Leu | Ser | Asp | Lys | Arg | Ser | Ile | Met | Gly |
| | | | 35 | | | | 40 | | | | | 45 | | | |
| Asn | Gln | Ser | Leu | Leu | Trp | Lys | Trp | Lys | Gly | Gly | Ser | Ser | Phe | Thr | Leu |
| | | 50 | | | | | 55 | | | | | 60 | | | |
| His | Lys | Lys | Leu | Ile | Val | Pro | Thr | Asp | Lys | Glu | Ala | Ser | Lys | Ala | Trp |
| 65 | | | | | 70 | | | | | 75 | | | | | 80 |

| Gly | Arg | Ser | Ser | Thr | Pro | Val | Phe | Ser | Phe | Trp | Leu | Tyr | Asn | Glu | Lys |
|---|---|---|---|---|---|---|---|---|---|---|---|---|---|---|---|
| | | | | 85 | | | | | 90 | | | | | | 95 |

| Pro | Ile | Asp | Gly | Tyr | Leu | Thr | Ile | Asp | Phe | Gly | Glu | Lys | Leu | Ile | Ser |
|---|---|---|---|---|---|---|---|---|---|---|---|---|---|---|---|
| | | | 100 | | | | 105 | | | | | 110 | | | |

| Thr | Ser | Glu | Ala | Gln | Ala | Gly | Phe | Lys | Val | Lys | Leu | Asp | Phe | Thr | Gly |
|---|---|---|---|---|---|---|---|---|---|---|---|---|---|---|---|
| | | 115 | | | | | 120 | | | | | 125 | | | |

| Trp | Arg | Ala | Val | Gly | Val | Ser | Leu | Asn | Asn | Asp | Leu | Glu | Asn | Arg | Glu |
|---|---|---|---|---|---|---|---|---|---|---|---|---|---|---|---|
| | 130 | | | | | 135 | | | | | 140 | | | | |

| Met | Thr | Leu | Asn | Ala | Thr | Asn | Ser | Ser | Asp | Gly | Thr | Gln | Asp | Ser |
|---|---|---|---|---|---|---|---|---|---|---|---|---|---|---|
| 145 | | | | | 150 | | | | | 155 | | | | 160 |

| Ile | Gly | Arg | Ser | Leu | Gly | Ala | Lys | Val | Asp | Ser | Ile | Arg | Phe | Lys | Ala |
|---|---|---|---|---|---|---|---|---|---|---|---|---|---|---|---|
| | | | | 165 | | | | | 170 | | | | | 175 | |

| Pro | Ser | Asn | Val | Ser | Gln | Gly | Glu | Ile | Tyr | Ile | Asp | Arg | Ile | Met | Phe |
|---|---|---|---|---|---|---|---|---|---|---|---|---|---|---|---|
| | | | 180 | | | | | 185 | | | | | 190 | | |

| Ser | Val | Asp | Asp | Ala | Arg | Tyr | Gln | Trp | Ser | Asp | Tyr | Gln | Val | Lys | Thr |
|---|---|---|---|---|---|---|---|---|---|---|---|---|---|---|---|
| | | 195 | | | | | 200 | | | | | 205 | | | |

| Arg | Leu | Ser | Glu | Pro | Glu | Ile | Gln | Phe | His | Asn | Val | Lys | Pro | Gln | Leu |
|---|---|---|---|---|---|---|---|---|---|---|---|---|---|---|---|
| | 210 | | | | | 215 | | | | | 220 | | | | |

| Pro | Val | Thr | Pro | Glu | Asn | Leu | Ala | Ala | Ile | Asp | Leu | Ile | Arg | Gln | Arg |
|---|---|---|---|---|---|---|---|---|---|---|---|---|---|---|---|
| 225 | | | | | 230 | | | | | 235 | | | | | 240 |

| Leu | Ile | Asn | Glu | Phe | Val | Gly | Gly | Glu | Lys | Glu | Thr | Asn | Leu | Ala | Leu |
|---|---|---|---|---|---|---|---|---|---|---|---|---|---|---|---|
| | | | | 245 | | | | | 250 | | | | | 255 | |

| Glu | Glu | Asn | Ile | Ser | Lys | Leu | Lys | Ser | Asp | Phe | Asp | Ala | Leu | Asn | Ile |
|---|---|---|---|---|---|---|---|---|---|---|---|---|---|---|---|
| | | | 260 | | | | | 265 | | | | | 270 | | |

| His | Thr | Leu | Ala | Asn | Gly | Gly | Thr | Gln | Gly | Arg | His | Leu | Ile | Thr | Asp |
|---|---|---|---|---|---|---|---|---|---|---|---|---|---|---|---|
| | | 275 | | | | | 280 | | | | | 285 | | | |

| Lys | Gln | Ile | Ile | Ile | Tyr | Gln | Pro | Glu | Asn | Leu | Asn | Ser | Gln | Asp | Lys |
|---|---|---|---|---|---|---|---|---|---|---|---|---|---|---|---|
| | 290 | | | | | 295 | | | | | 300 | | | | |

| Gln | Leu | Phe | Asp | Asn | Tyr | Val | Ile | Leu | Gly | Asn | Tyr | Thr | Thr | Leu | Met |
|---|---|---|---|---|---|---|---|---|---|---|---|---|---|---|---|
| 305 | | | | | 310 | | | | | 315 | | | | | 320 |

| Phe | Asn | Ile | Ser | Arg | Ala | Tyr | Val | Leu | Glu | Lys | Asp | Pro | Thr | Gln | Lys |
|---|---|---|---|---|---|---|---|---|---|---|---|---|---|---|---|
| | | | | 325 | | | | | 330 | | | | | 335 | |

| Ala | Gln | Leu | Lys | Gln | Met | Tyr | Leu | Leu | Met | Thr | Lys | His | Leu | Leu | Asp |
|---|---|---|---|---|---|---|---|---|---|---|---|---|---|---|---|
| | | | 340 | | | | | 345 | | | | | 350 | | |

| Gln | Gly | Phe | Val | Lys | Gly | Ser | Ala | Leu | Val | Thr | Thr | His | His | Trp | Gly |
|---|---|---|---|---|---|---|---|---|---|---|---|---|---|---|---|
| | | 355 | | | | | 360 | | | | | 365 | | | |

| Tyr | Ser | Ser | Arg | Trp | Trp | Tyr | Ile | Ser | Thr | Leu | Leu | Met | Ser | Asp | Ala |
|---|---|---|---|---|---|---|---|---|---|---|---|---|---|---|---|
| | 370 | | | | | 375 | | | | | 380 | | | | |

| Leu | Lys | Glu | Ala | Asn | Leu | Gln | Thr | Gln | Val | Tyr | Asp | Ser | Leu | Leu | Trp |
|---|---|---|---|---|---|---|---|---|---|---|---|---|---|---|---|
| 385 | | | | | 390 | | | | | 395 | | | | | 400 |

| Tyr | Ser | Arg | Glu | Phe | Lys | Ser | Ser | Phe | Asp | Met | Lys | Val | Ser | Ala | Asp |
|---|---|---|---|---|---|---|---|---|---|---|---|---|---|---|---|
| | | | | 405 | | | | | 410 | | | | | 415 | |

| Ser | Ser | Asp | Leu | Asp | Tyr | Phe | Asn | Thr | Leu | Ser | Arg | Gln | His | Leu | Ala |
|---|---|---|---|---|---|---|---|---|---|---|---|---|---|---|---|
| | | | 420 | | | | | 425 | | | | | 430 | | |

| Leu | Leu | Leu | Leu | Glu | Pro | Asp | Asp | Gln | Lys | Arg | Ile | Asn | Leu | Val | Asn |
|---|---|---|---|---|---|---|---|---|---|---|---|---|---|---|---|
| | | | 435 | | | | | 440 | | | | | 445 | | |

| Thr | Phe | Ser | His | Tyr | Ile | Thr | Gly | Ala | Leu | Thr | Gln | Val | Pro | Pro | Gly |
|---|---|---|---|---|---|---|---|---|---|---|---|---|---|---|---|
| | 450 | | | | | 455 | | | | | 460 | | | | |

| Gly | Lys | Asp | Gly | Leu | Arg | Pro | Asp | Gly | Thr | Ala | Trp | Arg | His | Glu | Gly |
|---|---|---|---|---|---|---|---|---|---|---|---|---|---|---|---|
| 465 | | | | | 470 | | | | | 475 | | | | | 480 |

| Asn | Tyr | Pro | Gly | Tyr | Ser | Phe | Pro | Ala | Phe | Lys | Asn | Ala | Ser | Gln | Leu |
|---|---|---|---|---|---|---|---|---|---|---|---|---|---|---|---|
| | | | | 485 | | | | | 490 | | | | | 495 | |

| Ile | Tyr | Leu | Leu | Arg | Asp | Thr | Pro | Phe | Ser | Val | Gly | Glu | Ser | Gly | Trp |
|---|---|---|---|---|---|---|---|---|---|---|---|---|---|---|---|
| | | | 500 | | | | | 505 | | | | | 510 | | |

Asn Asn Leu Lys Lys Ala Met Val Ser Ala Trp Ile Tyr Ser Asn Pro
            515                 520                 525

Glu Val Gly Leu Pro Leu Ala Gly Arg His Pro Phe Asn Ser Pro Ser
        530                 535                 540

Leu Lys Ser Val Ala Gln Gly Tyr Tyr Trp Leu Ala Met Ser Ala Lys
545                 550                 555                 560

Ser Ser Pro Asp Lys Thr Leu Ala Ser Ile Tyr Leu Ala Ile Ser Asp
                565                 570                 575

Lys Thr Gln Asn Glu Ser Thr Ala Ile Phe Gly Glu Thr Ile Thr Pro
            580                 585                 590

Ala Ser Leu Pro Gln Gly Phe Tyr Ala Phe Asn Gly Gly Ala Phe Gly
        595                 600                 605

Ile His Arg Trp Gln Asp Lys Met Val Thr Leu Lys Ala Tyr Asn Thr
    610                 615                 620

Asn Val Trp Ser Ser Glu Ile Tyr Asn Lys Asp Asn Arg Tyr Gly Arg
625                 630                 635                 640

Tyr Gln Ser His Gly Val Ala Gln Ile Val Ser Asn Gly Ser Gln Leu
            645                 650                 655

Ser Gln Gly Tyr Gln Gln Glu Gly Trp Asp Trp Asn Arg Met Gln Gly
        660                 665                 670

Ala Thr Thr Ile His Leu Pro Leu Lys Asp Leu Asp Ser Pro Lys Pro
    675                 680                 685

His Thr Leu Met Gln Arg Gly Glu Arg Gly Phe Ser Gly Thr Ser Ser
    690                 695                 700

Leu Glu Gly Gln Tyr Gly Met Met Ala Phe Asp Leu Ile Tyr Pro Ala
705                 710                 715                 720

Asn Leu Glu Arg Phe Asp Pro Asn Phe Thr Ala Lys Lys Ser Val Leu
                725                 730                 735

Ala Ala Asp Asn His Leu Ile Phe Ile Gly Ser Asn Ile Asn Ser Ser
            740                 745                 750

Asp Lys Asn Lys Asn Val Glu Thr Thr Leu Phe Gln His Ala Ile Thr
        755                 760                 765

Pro Thr Leu Asn Thr Leu Trp Ile Asn Gly Gln Lys Ile Glu Asn Met
    770                 775                 780

Pro Tyr Gln Thr Thr Leu Gln Gln Gly Asp Trp Leu Ile Asp Ser Asn
785                 790                 795                 800

Gly Asn Gly Tyr Leu Ile Thr Gln Ala Glu Lys Val Asn Val Ser Arg
                805                 810                 815

Gln His Gln Val Ser Ala Glu Asn Lys Asn Arg Gln Pro Thr Glu Gly
            820                 825                 830

Asn Phe Ser Ser Ala Trp Ile Asp His Ser Thr Arg Pro Lys Asp Ala
        835                 840                 845

Ser Tyr Glu Tyr Met Val Phe Leu Asp Ala Thr Pro Glu Lys Met Gly
    850                 855                 860

Glu Met Ala Gln Lys Phe Arg Glu Asn Asn Gly Leu Tyr Gln Val Leu
865                 870                 875                 880

Arg Lys Asp Lys Asp Val His Ile Ile Leu Asp Lys Leu Ser Asn Val
                885                 890                 895

Thr Gly Tyr Ala Phe Tyr Gln Pro Ala Ser Ile Glu Asp Lys Trp Ile
            900                 905                 910

Lys Lys Val Asn Lys Pro Ala Ile Val Met Thr His Arg Gln Lys Asp
        915                 920                 925

Thr Leu Ile Val Ser Ala Val Thr Pro Asp Leu Asn Met Thr Arg Gln

|  |  |  |  |  |  |  |  |  |  |  |  |  |
|---|---|---|---|---|---|---|---|---|---|---|---|---|
|  |  | 930 |  |  | 935 |  |  |  | 940 |  |  |  |
| Lys | Ala | Ala | Thr | Pro | Val | Thr | Ile | Asn | Val | Thr | Ile | Asn | Gly | Lys | Trp |
| 945 |  |  |  |  | 950 |  |  |  | 955 |  |  |  |  |  | 960 |
| Gln | Ser | Ala | Asp | Lys | Asn | Ser | Glu | Val | Lys | Tyr | Gln | Val | Ser | Gly | Asp |
|  |  |  |  | 965 |  |  |  |  | 970 |  |  |  |  | 975 |  |
| Asn | Thr | Glu | Leu | Thr | Phe | Thr | Ser | Tyr | Phe | Gly | Ile | Pro | Gln | Glu | Ile |
|  |  |  | 980 |  |  |  |  | 985 |  |  |  |  | 990 |  |  |
| Lys | Leu | Ser | Pro | Leu | Pro |
|  |  | 995 |

( 2 ) INFORMATION FOR SEQ ID NO:7:

( i ) SEQUENCE CHARACTERISTICS:
        ( A ) LENGTH: 6519 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 3238..6276

( x i ) SEQUENCE DESCRIPTION: SEQ ID NO:7:

```
GGAATTCCAT CACTCAATCA TTAAATTTAG GCACAACGAT GGGCTATCAG CGTTATGACA      60
AATTTAATGA AGGACGCATT GGTTTCACTG TTAGCCAGCG TTTCTAAGGA GAAAATAAT     120
GCCGATATTT CGTTTTACTG CACTTGCAAT GACATTGGGG CTATTATCAG CGCCTTATAA    180
CGCGATGGCA GCCACCAGCA ATCCTGCATT TGATCCTAAA AATCTGATGC AGTCAGAAAT    240
TTACCATTTT GCACAAAATA ACCCATTAGC AGACTTCTCA TCAGATAAAA ACTCAATACT    300
AACGTTATCT GATAAACGTA GCATTATGGG AAACCAATCT CTTTATGGA ATGGAAAGG     360
TGGTAGTAGC TTTACTTTAC ATAAAAAACT GATTGTCCCC ACCGATAAAG AAGCATCTAA    420
AGCATGGGGA CGCTCATCTA CCCCCGTTTT CTCATTTTGG CTTTACAATG AAAAACCGAT    480
TGATGGTTAT CTTACTATCG ATTTCGGAGA AAAACTCATT TCAACCAGTG AGGCTCAGGC    540
AGGCTTTAAA GTAAAATTAG ATTTCACTGG CTGGCGTGCT GTGGGAGTCT CTTTAAATAA    600
CGATCTTGAA AATCGAGAGA TGACCTTAAA TGCAACCAAT ACCTCCTCTG ATGGTACTCA    660
AGACAGCATT GGGCGTTCTT TAGGTGCTAA AGTCGATAGT ATTCGTTTTA AAGCGCCTTC    720
TAATGTGAGT CAGGGTGAAA TCTATATCGA CCGTATTATG TTTTCTGTCG ATGATGCTCG    780
CTACCAATGG TCTGATTATC AAGTAAAAAC TCGCTTATCA GAACCTGAAA TTCAATTTCA    840
CAACGTAAAG CCACAACTAC CTGTAACACC TGAAAATTTA GCGGCCATTG ATCTTATTCG    900
CCAACGTCTA ATTAATGAAT TTGTCGGAGG TGAAAAGAG ACAAACCTCG CATTAGAAGA    960
GAATATCAGC AAATTAAAAA GTGATTTCGA TGCTCTTAAT ATTCACACTT TAGCAAATGG   1020
TGGAACGCAA GGCAGACATC TGATCACTGA TAAACAAATC ATTATTTATC AACCAGAGAA   1080
TCTTAACTCC CAAGATAAAC AACTATTTGA TAATTATGTT ATTTTAGGTA ATTACACGAC   1140
ATTAATGTTT AATATTAGCC GTGCTTATGT GCTGGAAAAA GATCCCACAC AAAAGGCGCA   1200
ACTAAAGCAG ATGTACTTAT TAATGACAAA GCATTATTA GATCAAGGCT TTGTTAAAGG    1260
GAGTGCTTTA GTGACAACCC ATCACTGGGG ATACAGTTCT CGTTGGTGGT ATATTTCCAC   1320
GTTATTAATG TCTGATGCAC TAAAAGAAGC GAACCTACAA ACTCAAGTTT ATGATTCATT   1380
```

| | |
|---|---|
| ACTGTGGTAT TCACGTGAGT TTAAAAGTAG TTTTGATATG AAAGTAAGTG CTGATAGCTC | 1440 |
| TGATCTAGAT TATTTCAATA CCTTATCTCG CCAACATTTA GCCTTATTAT TACTAGAGCC | 1500 |
| TGATGATCAA AAGCGTATCA ACTTAGTTAA TACTTTCAGC CATTATATCA CTGGCGCATT | 1560 |
| AACGCAAGTG CCACCGGGTG GTAAAGATGG TTTACGCCCT GATGGTACAG CATGGCGACA | 1620 |
| TGAAGGCAAC TATCCGGGCT ACTCTTTCCC AGCCTTTAAA AATGCCTCTC AGCTTATTTA | 1680 |
| TTTATTACGC GATACACCAT TTCAGTGGG TGAAAGTGGT TGGAATAACC TGAAAAAGC | 1740 |
| GATGGTTTCA GCGTGGATCT ACAGTAATCC AGAAGTTGGA TTACCGCTTG CAGGAAGACA | 1800 |
| CCCTTTTAAC TCACCTTCGT TAAAATCAGT CGCTCAAGGC TATTACTGGC TTGCCATGTC | 1860 |
| TGCAAAATCA TCGCCTGATA AACACTTGC ATCTATTTAT CTTGCGATTA GTGATAAAAC | 1920 |
| ACAAAATGAA TCAACTGCTA TTTTTGGAGA AACTATTACA CCAGCGTCTT TACCTCAAGG | 1980 |
| TTTCTATGCC TTTAATGGCG GTGCTTTTGG TATTCATCGT TGGCAAGATA AATGGTGAC | 2040 |
| ACTGAAAGCT TATAACACCA ATGTTTGGTC ATCTGAAATT TATAACAAAG ATAACCGTTA | 2100 |
| TGGCCGTTAC CAAAGTCATG GTGTCGCTCA AATAGTGAGT AATGGCTCGC AGCTTTCACA | 2160 |
| GGGCTATCAG CAAGAAGGTT GGGATTGGAA TAGAATGCAA GGGGCAACCA CTATTCACCT | 2220 |
| TCCTCTTAAA GACTTAGACA GTCCTAAACC TCATACCTTA ATGCAACGTG GAGAGCGTGG | 2280 |
| ATTTAGCGGA ACATCATCCC TTGAAGGTCA ATATGGCATG ATGGCATTCG ATCTTATTTA | 2340 |
| TCCCGCCAAT CTTGAGCGTT TTGATCCTAA TTTCACTGCG AAAAAGAGTG TATTAGCCGC | 2400 |
| TGATAATCAC TTAATTTTTA TTGGTAGCAA TATAAATAGT AGTGATAAAA ATAAAAATGT | 2460 |
| TGAAACGACC TTATTCCAAC ATGCCATTAC TCCAACATTA AATACCCTTT GGATTAATGG | 2520 |
| ACAAAGATA GAAAACATGC CTTATCAAAC AACACTTCAA CAAGGTGATT GGTTAATTGA | 2580 |
| TAGCAATGGC AATGGTTACT TAATTACTCA AGCAGAAAAA GTAAATGTAA GTCGCCAACA | 2640 |
| TCAGGTTTCA GCGGAAAATA AAAATCGCCA ACCGACAGAA GGAAACTTTA GCTCGGCATG | 2700 |
| GATCGATCAC AGCACTCGCC CCAAAGATGC CAGTTATGAG TATATGGTCT TTTTAGATGC | 2760 |
| GACACCTGAA AAAATGGGAG AGATGGCACA AAAATTCCGT GAAAATAATG GGTTATATCA | 2820 |
| GGTTCTTCGT AAGGATAAAG ACGTTCATAT TATTCTCGAT AAACTCAGCA ATGTAACGGG | 2880 |
| ATATGCCTTT TATCAGCCAG CATCAATTGA AGACAAATGG ATCAAAAAGG TTAATAAACC | 2940 |
| TGCAATTGTG ATGACTCATC GACAAAAAGA CACTCTTATT GTCAGTGCAG TTACACCTGA | 3000 |
| TTTAAATATG ACTCGCCAAA AAGCAGCAAC TCCTGTCACC ATCAATGTCA CGATTAATGG | 3060 |
| CAAATGGCAA TCTGCTGATA AAAATAGTGA AGTGAAATAT CAGGTTTCTG GTGATAACAC | 3120 |
| TGAACTGACG TTTACGAGTT ACTTTGGTAT TCCACAAGAA ATCAAACTCT CGCCACTCCC | 3180 |
| TTGATTTAAT CAAAAGAACG CTCTTGCGTT CCTTTTTTAT TTGCAGGAAA TCTGATT | 3237 |

| | | | | | | | | | | | | | | | | |
|---|---|---|---|---|---|---|---|---|---|---|---|---|---|---|---|---|
| ATG | CTA | ATA | AAA | AAC | CCT | TTA | GCC | CAC | GCG | GTT | ACA | TTA | AGC | CTC | TGT | 3285 |
| Met | Leu | Ile | Lys | Asn | Pro | Leu | Ala | His | Ala | Val | Thr | Leu | Ser | Leu | Cys | |
| 1 | | | | 5 | | | | | 10 | | | | | 15 | | |
| TTA | TCA | TTA | CCC | GCA | CAA | GCA | TTA | CCC | ACT | CTG | TCT | CAT | GAA | GCT | TTC | 3333 |
| Leu | Ser | Leu | Pro | Ala | Gln | Ala | Leu | Pro | Thr | Leu | Ser | His | Glu | Ala | Phe | |
| | | | 20 | | | | | 25 | | | | | 30 | | | |
| GGC | GAT | ATT | TAT | CTT | TTT | GAA | GGT | GAA | TTA | CCC | AAT | ACC | CTT | ACC | ACT | 3381 |
| Gly | Asp | Ile | Tyr | Leu | Phe | Glu | Gly | Glu | Leu | Pro | Asn | Thr | Leu | Thr | Thr | |
| | | 35 | | | | 40 | | | | | 45 | | | | | |
| TCA | AAT | AAT | AAT | CAA | TTA | TCG | CTA | AGC | AAA | CAG | CAT | GCT | AAA | GAT | GGT | 3429 |
| Ser | Asn | Asn | Asn | Gln | Leu | Ser | Leu | Ser | Lys | Gln | His | Ala | Lys | Asp | Gly | |
| | 50 | | | | 55 | | | | | 60 | | | | | | |
| GAA | CAA | TCA | CTC | AAA | TGG | CAA | TAT | CAA | CCA | CAA | GCA | ACA | TTA | ACA | CTA | 3477 |

| | | | | | | | | | | | | | | | |
|---|---|---|---|---|---|---|---|---|---|---|---|---|---|---|---|
| Glu | Gln | Ser | Leu | Lys | Trp | Gln | Tyr | Gln | Pro | Gln | Ala | Thr | Leu | Thr | Leu |
| 65 | | | | 70 | | | | 75 | | | | | | 80 | |

| | | | | | | | | | | | | | | | |
|---|---|---|---|---|---|---|---|---|---|---|---|---|---|---|---|
| AAT | AAT | ATT | GTT | AAT | TAC | CAA | GAT | GAT | AAA | AAT | ACA | GCC | ACA | CCA | CTC | 3525 |
| Asn | Asn | Ile | Val | Asn | Tyr | Gln | Asp | Asp | Lys | Asn | Thr | Ala | Thr | Pro | Leu |
| | | | | 85 | | | | | 90 | | | | | 95 | |

ACT TTT ATG ATG TGG ATT TAT AAT GAA AAA CCT CAA TCT TCC CCA TTA   3573
Thr Phe Met Met Trp Ile Tyr Asn Glu Lys Pro Gln Ser Ser Pro Leu
            100                 105                 110

ACG TTA GCA TTT AAA CAA AAT AAT AAA ATT GCA CTA AGT TTT AAT GCT   3621
Thr Leu Ala Phe Lys Gln Asn Asn Lys Ile Ala Leu Ser Phe Asn Ala
        115                 120                 125

GAA CTT AAT TTT ACG GGG TGG CGA GGT ATT GCT GTT CCT TTT CGT GAT   3669
Glu Leu Asn Phe Thr Gly Trp Arg Gly Ile Ala Val Pro Phe Arg Asp
    130                 135                 140

ATG CAA GGC TCT GCG ACA GGT CAA CTT GAT CAA TTA GTG ATC ACC GCT   3717
Met Gln Gly Ser Ala Thr Gly Gln Leu Asp Gln Leu Val Ile Thr Ala
145                 150                 155                 160

CCA AAC CAA GCC GGA ACA CTC TTT TTT GAT CAA ATC ATC ATG AGT GTA   3765
Pro Asn Gln Ala Gly Thr Leu Phe Phe Asp Gln Ile Ile Met Ser Val
                165                 170                 175

CCG TTA GAC AAT CGT TGG GCA GTA CCT GAC TAT CAA ACA CCT TAC GTA   3813
Pro Leu Asp Asn Arg Trp Ala Val Pro Asp Tyr Gln Thr Pro Tyr Val
            180                 185                 190

AAT AAC GCA GTA AAC ACG ATG GTT AGT AAA AAC TGG AGT GCA TTA TTG   3861
Asn Asn Ala Val Asn Thr Met Val Ser Lys Asn Trp Ser Ala Leu Leu
        195                 200                 205

ATG TAC GAT CAG ATG TTT CAA GCC CAT TAC CCT ACT TTA AAC TTC GAT   3909
Met Tyr Asp Gln Met Phe Gln Ala His Tyr Pro Thr Leu Asn Phe Asp
    210                 215                 220

ACT GAA TTT CGC GAT GAC CAA ACA GAA ATG GCT TCG ATT TAT CAG CGC   3957
Thr Glu Phe Arg Asp Asp Gln Thr Glu Met Ala Ser Ile Tyr Gln Arg
225                 230                 235                 240

TTT GAA TAT TAT CAA GGA ATT CGT AGT GAT AAA AAA ATT ACT CCA GAT   4005
Phe Glu Tyr Tyr Gln Gly Ile Arg Ser Asp Lys Lys Ile Thr Pro Asp
                245                 250                 255

ATG CTA GAT AAA CAT TTA GCA TTA TGG GAA AAA TTG GTG TTA ACA CAA   4053
Met Leu Asp Lys His Leu Ala Leu Trp Glu Lys Leu Val Leu Thr Gln
            260                 265                 270

CAC GCT GAT GGC TCA ATC ACA GGA AAA GCC CTT GAT CAC CCT AAC CGG   4101
His Ala Asp Gly Ser Ile Thr Gly Lys Ala Leu Asp His Pro Asn Arg
        275                 280                 285

CAA CAT TTT ATG AAA GTC GAA GGT GTA TTT AGT GAG GGG ACT CAA AAA   4149
Gln His Phe Met Lys Val Glu Gly Val Phe Ser Glu Gly Thr Gln Lys
    290                 295                 300

GCA TTA CTT GAT GCC AAT ATG CTA AGA GAT GTG GGC AAA ACG CTT CTT   4197
Ala Leu Leu Asp Ala Asn Met Leu Arg Asp Val Gly Lys Thr Leu Leu
305                 310                 315                 320

CAA ACT GCT ATT TAC TTG CGT AGC GAT TCA TTA TCA GCA ACT GAT AGA   4245
Gln Thr Ala Ile Tyr Leu Arg Ser Asp Ser Leu Ser Ala Thr Asp Arg
                325                 330                 335

AAA AAA TTA GAA GAG CGC TAT TTA TTA GGT ACT CGT TAT GTC CTT GAA   4293
Lys Lys Leu Glu Glu Arg Tyr Leu Leu Gly Thr Arg Tyr Val Leu Glu
            340                 345                 350

CAA GGT TTT ACA CGA GGA AGT GGT TAT CAA ATT ATT ACT CAT GTT GGT   4341
Gln Gly Phe Thr Arg Gly Ser Gly Tyr Gln Ile Ile Thr His Val Gly
        355                 360                 365

TAC CAA ACC AGA GAA CTT TTT GAT GCA TGG TTT ATT GGC CGT CAT GTT   4389
Tyr Gln Thr Arg Glu Leu Phe Asp Ala Trp Phe Ile Gly Arg His Val
    370                 375                 380

CTT GCA AAA AAT AAC CTT TTA GCC CCC ACT CAA CAA GCT ATG ATG TGG   4437

| | | | | | | | | | | | | | | | |
|---|---|---|---|---|---|---|---|---|---|---|---|---|---|---|---|
| Leu | Ala | Lys | Asn | Asn | Leu | Leu | Ala | Pro | Thr | Gln | Gln | Ala | Met | Met | Trp |
| 385 | | | | | 390 | | | | | 395 | | | | | 400 |

| TAC | AAC | GCC | ACA | GGA | CGT | ATT | TTT | GAA | AAA | AAT | AAT | GAA | ATT | GTT | GAT | 4485 |
|---|---|---|---|---|---|---|---|---|---|---|---|---|---|---|---|---|
| Tyr | Asn | Ala | Thr | Gly | Arg | Ile | Phe | Glu | Lys | Asn | Asn | Glu | Ile | Val | Asp | |
| | | | | 405 | | | | | 410 | | | | | 415 | | |

| GCA | AAT | GTC | GAT | ATT | CTC | AAT | ACT | CAA | TTG | CAA | TGG | ATG | ATA | AAA | AGC | 4533 |
|---|---|---|---|---|---|---|---|---|---|---|---|---|---|---|---|---|
| Ala | Asn | Val | Asp | Ile | Leu | Asn | Thr | Gln | Leu | Gln | Trp | Met | Ile | Lys | Ser | |
| | | | 420 | | | | | 425 | | | | | 430 | | | |

| TTA | TTG | ATG | CTA | CCG | GAT | TAT | CAA | CAA | CGT | CAA | CAA | GCC | TTA | GCG | CAA | 4581 |
|---|---|---|---|---|---|---|---|---|---|---|---|---|---|---|---|---|
| Leu | Leu | Met | Leu | Pro | Asp | Tyr | Gln | Gln | Arg | Gln | Gln | Ala | Leu | Ala | Gln | |
| | | 435 | | | | | 440 | | | | | 445 | | | | |

| CTG | CAA | AGT | TGG | CTA | AAT | AAA | ACC | ATT | CTA | AGC | TCA | AAA | GGT | GTT | GCT | 4629 |
|---|---|---|---|---|---|---|---|---|---|---|---|---|---|---|---|---|
| Leu | Gln | Ser | Trp | Leu | Asn | Lys | Thr | Ile | Leu | Ser | Ser | Lys | Gly | Val | Ala | |
| | 450 | | | | | 455 | | | | | 460 | | | | | |

| GGC | GGT | TTC | AAA | TCT | GAT | GGT | TCT | ATT | TTT | CAC | CAT | TCA | CAA | CAT | TAC | 4677 |
|---|---|---|---|---|---|---|---|---|---|---|---|---|---|---|---|---|
| Gly | Gly | Phe | Lys | Ser | Asp | Gly | Ser | Ile | Phe | His | His | Ser | Gln | His | Tyr | |
| 465 | | | | | 470 | | | | | 475 | | | | | 480 | |

| CCC | GCT | TAT | GCT | AAA | GAT | GCA | TTT | GGT | GGT | TTA | GCA | CCC | AGT | GTT | TAT | 4725 |
|---|---|---|---|---|---|---|---|---|---|---|---|---|---|---|---|---|
| Pro | Ala | Tyr | Ala | Lys | Asp | Ala | Phe | Gly | Gly | Leu | Ala | Pro | Ser | Val | Tyr | |
| | | | | 485 | | | | | 490 | | | | | 495 | | |

| GCA | TTA | AGT | GAT | TCA | CCT | TTT | CGC | TTA | TCT | ACT | TCA | GCA | CAT | GAG | CGT | 4773 |
|---|---|---|---|---|---|---|---|---|---|---|---|---|---|---|---|---|
| Ala | Leu | Ser | Asp | Ser | Pro | Phe | Arg | Leu | Ser | Thr | Ser | Ala | His | Glu | Arg | |
| | | | 500 | | | | | 505 | | | | | 510 | | | |

| TTA | AAA | GAT | GTT | TTG | TTA | AAA | ATG | CGG | ATC | TAC | ACC | AAA | GAG | ACA | CAA | 4821 |
|---|---|---|---|---|---|---|---|---|---|---|---|---|---|---|---|---|
| Leu | Lys | Asp | Val | Leu | Leu | Lys | Met | Arg | Ile | Tyr | Thr | Lys | Glu | Thr | Gln | |
| | | 515 | | | | | 520 | | | | | 525 | | | | |

| ATT | CCT | GTG | GTA | TTA | AGT | GGT | CGT | CAT | CCA | ACT | GGG | TTG | CAT | AAA | ATA | 4869 |
|---|---|---|---|---|---|---|---|---|---|---|---|---|---|---|---|---|
| Ile | Pro | Val | Val | Leu | Ser | Gly | Arg | His | Pro | Thr | Gly | Leu | His | Lys | Ile | |
| | 530 | | | | | 535 | | | | | 540 | | | | | |

| GGG | ATC | GCG | CCA | TTT | AAA | TGG | ATG | GCA | TTA | GCA | GGA | ACC | CCA | GAT | GGC | 4917 |
|---|---|---|---|---|---|---|---|---|---|---|---|---|---|---|---|---|
| Gly | Ile | Ala | Pro | Phe | Lys | Trp | Met | Ala | Leu | Ala | Gly | Thr | Pro | Asp | Gly | |
| 545 | | | | | 550 | | | | | 555 | | | | | 560 | |

| AAA | CAA | AAG | TTA | GAT | ACC | ACA | TTA | TCC | GCC | GCT | TAT | GCA | AAA | TTA | GAC | 4965 |
|---|---|---|---|---|---|---|---|---|---|---|---|---|---|---|---|---|
| Lys | Gln | Lys | Leu | Asp | Thr | Thr | Leu | Ser | Ala | Ala | Tyr | Ala | Lys | Leu | Asp | |
| | | | | 565 | | | | | 570 | | | | | 575 | | |

| AAC | AAA | ACG | CAT | TTT | GAA | GGC | ATT | AAC | GCT | GAA | AGT | GAG | CCA | GTC | GGC | 5013 |
|---|---|---|---|---|---|---|---|---|---|---|---|---|---|---|---|---|
| Asn | Lys | Thr | His | Phe | Glu | Gly | Ile | Asn | Ala | Glu | Ser | Glu | Pro | Val | Gly | |
| | | | 580 | | | | | 585 | | | | | 590 | | | |

| GCA | TGG | GCA | ATG | AAT | TAT | GCA | TCA | ATG | GCA | ATA | CAA | CGA | AGA | GCA | TCG | 5061 |
|---|---|---|---|---|---|---|---|---|---|---|---|---|---|---|---|---|
| Ala | Trp | Ala | Met | Asn | Tyr | Ala | Ser | Met | Ala | Ile | Gln | Arg | Arg | Ala | Ser | |
| | | 595 | | | | | 600 | | | | | 605 | | | | |

| ACC | CAA | TCA | CCA | CAA | CAA | AGC | TGG | CTC | GCC | ATA | GCG | CGC | GGT | TTT | AGC | 5109 |
|---|---|---|---|---|---|---|---|---|---|---|---|---|---|---|---|---|
| Thr | Gln | Ser | Pro | Gln | Gln | Ser | Trp | Leu | Ala | Ile | Ala | Arg | Gly | Phe | Ser | |
| | 610 | | | | | 615 | | | | | 620 | | | | | |

| CGT | TAT | CTT | GTT | GGT | AAT | GAA | AGC | TAT | GAA | AAT | AAC | AAC | CGT | TAT | GGT | 5157 |
|---|---|---|---|---|---|---|---|---|---|---|---|---|---|---|---|---|
| Arg | Tyr | Leu | Val | Gly | Asn | Glu | Ser | Tyr | Glu | Asn | Asn | Asn | Arg | Tyr | Gly | |
| 625 | | | | | 630 | | | | | 635 | | | | | 640 | |

| CGT | TAT | TTA | CAA | TAT | GGA | CAA | TTG | GAA | ATT | ATT | CCA | GCT | GAT | TTA | ACT | 5205 |
|---|---|---|---|---|---|---|---|---|---|---|---|---|---|---|---|---|
| Arg | Tyr | Leu | Gln | Tyr | Gly | Gln | Leu | Glu | Ile | Ile | Pro | Ala | Asp | Leu | Thr | |
| | | | | 645 | | | | | 650 | | | | | 655 | | |

| CAA | TCA | GGG | TTT | AGC | CAT | GCT | GGA | TGG | GAT | TGG | AAT | AGA | TAT | CCA | GGT | 5253 |
|---|---|---|---|---|---|---|---|---|---|---|---|---|---|---|---|---|
| Gln | Ser | Gly | Phe | Ser | His | Ala | Gly | Trp | Asp | Trp | Asn | Arg | Tyr | Pro | Gly | |
| | | | 660 | | | | | 665 | | | | | 670 | | | |

| ACA | ACA | ACT | ATT | CAT | CTT | CCC | TAT | AAC | GAA | CTT | GAA | GCA | AAA | CTT | AAT | 5301 |
|---|---|---|---|---|---|---|---|---|---|---|---|---|---|---|---|---|
| Thr | Thr | Thr | Ile | His | Leu | Pro | Tyr | Asn | Glu | Leu | Glu | Ala | Lys | Leu | Asn | |
| | | 675 | | | | | 680 | | | | | 685 | | | | |

| CAA | TTA | CCT | GCT | GCA | GGT | ATT | GAA | GAA | ATG | TTG | CTT | TCA | ACA | GAA | AGT | 5349 |
|---|---|---|---|---|---|---|---|---|---|---|---|---|---|---|---|---|
| Gln | Leu | Pro | Ala | Ala | Gly | Ile | Glu | Glu | Met | Leu | Leu | Ser | Thr | Glu | Ser | |
| | 690 | | | | | 695 | | | | | 700 | | | | | |

| TAC | TCT | GGT | GCA | AAT | ACC | CTT | AAT | AAT | AAC | AGT | ATG | TTT | GCC | ATG | AAA | 5397 |

| | | | | | | | | | | | | | | | | |
|---|---|---|---|---|---|---|---|---|---|---|---|---|---|---|---|---|
| Tyr | Ser | Gly | Ala | Asn | Thr | Leu | Asn | Asn | Asn | Ser | Met | Phe | Ala | Met | Lys | |
| 705 | | | | | 710 | | | | | 715 | | | | | 720 | |
| TTA | CAC | GGT | CAC | AGT | AAA | TAT | CAA | CAA | CAA | AGC | TTA | AGG | GCA | AAT | AAA | 5445 |
| Leu | His | Gly | His | Ser | Lys | Tyr | Gln | Gln | Gln | Ser | Leu | Arg | Ala | Asn | Lys | |
| | | | | 725 | | | | | 730 | | | | | 735 | | |
| TCC | TAT | TTC | TTA | TTT | GAT | AAT | AGA | GTT | ATT | GCT | TTA | GGC | TCA | GGT | ATT | 5493 |
| Ser | Tyr | Phe | Leu | Phe | Asp | Asn | Arg | Val | Ile | Ala | Leu | Gly | Ser | Gly | Ile | |
| | | | 740 | | | | | 745 | | | | | 750 | | | |
| GAA | AAT | GAT | GAT | AAA | CAA | CAT | ACG | ACC | GAA | ACA | ACA | CTA | TTC | CAG | TTT | 5541 |
| Glu | Asn | Asp | Asp | Lys | Gln | His | Thr | Thr | Glu | Thr | Thr | Leu | Phe | Gln | Phe | |
| | | 755 | | | | | 760 | | | | | 765 | | | | |
| GCC | GTC | CCT | AAA | TTA | CAG | TCA | GTG | ATC | ATT | AAT | GGC | AAA | AAG | GTA | AAT | 5589 |
| Ala | Val | Pro | Lys | Leu | Gln | Ser | Val | Ile | Ile | Asn | Gly | Lys | Lys | Val | Asn | |
| | 770 | | | | | 775 | | | | | 780 | | | | | |
| CAA | TTA | GAT | ACT | CAA | TTA | ACT | TTA | AAT | AAT | GCA | GAT | ACA | TTA | ATT | GAT | 5637 |
| Gln | Leu | Asp | Thr | Gln | Leu | Thr | Leu | Asn | Asn | Ala | Asp | Thr | Leu | Ile | Asp | |
| 785 | | | | | 790 | | | | | 795 | | | | | 800 | |
| CCT | GCC | GGC | AAT | TTA | TAT | AAG | CTC | ACT | AAA | GGA | CAA | ACT | GTA | AAA | TTT | 5685 |
| Pro | Ala | Gly | Asn | Leu | Tyr | Lys | Leu | Thr | Lys | Gly | Gln | Thr | Val | Lys | Phe | |
| | | | | 805 | | | | | 810 | | | | | 815 | | |
| AGT | TAT | CAA | AAA | CAA | CAT | TCA | CTT | GAT | GAT | AGA | AAT | TCA | AAA | CCA | ACA | 5733 |
| Ser | Tyr | Gln | Lys | Gln | His | Ser | Leu | Asp | Asp | Arg | Asn | Ser | Lys | Pro | Thr | |
| | | | 820 | | | | | 825 | | | | | 830 | | | |
| GAA | CAA | TTA | TTT | GCA | ACA | GCT | GTT | ATT | TCT | CAT | GGT | AAG | GCA | CCG | AGT | 5781 |
| Glu | Gln | Leu | Phe | Ala | Thr | Ala | Val | Ile | Ser | His | Gly | Lys | Ala | Pro | Ser | |
| | | 835 | | | | | 840 | | | | | 845 | | | | |
| AAT | GAA | AAT | TAT | GAA | TAT | GCA | ATA | GCT | ATC | GAA | GCA | CAA | AAT | AAT | AAA | 5829 |
| Asn | Glu | Asn | Tyr | Glu | Tyr | Ala | Ile | Ala | Ile | Glu | Ala | Gln | Asn | Asn | Lys | |
| | 850 | | | | | 855 | | | | | 860 | | | | | |
| GCT | CCC | GAA | TAC | ACA | GTA | TTA | CAA | CAT | AAT | GAT | CAG | CTC | CAT | GCG | GTA | 5877 |
| Ala | Pro | Glu | Tyr | Thr | Val | Leu | Gln | His | Asn | Asp | Gln | Leu | His | Ala | Val | |
| 865 | | | | | 870 | | | | | 875 | | | | | 880 | |
| AAA | GAT | AAA | ATA | ACC | CAA | GAA | GAG | GGA | TAT | GCT | TTT | TTT | GAA | GCC | ACT | 5925 |
| Lys | Asp | Lys | Ile | Thr | Gln | Glu | Glu | Gly | Tyr | Ala | Phe | Phe | Glu | Ala | Thr | |
| | | | | 885 | | | | | 890 | | | | | 895 | | |
| AAG | TTA | AAA | TCA | GCG | GAT | GCA | ACA | TTA | TTA | TCC | AGT | GAT | GCG | CCG | GTT | 5973 |
| Lys | Leu | Lys | Ser | Ala | Asp | Ala | Thr | Leu | Leu | Ser | Ser | Asp | Ala | Pro | Val | |
| | | | 900 | | | | | 905 | | | | | 910 | | | |
| ATG | GTC | ATG | GCT | AAA | ATA | CAA | AAT | CAG | CAA | TTA | ACA | TTA | AGT | ATT | GTT | 6021 |
| Met | Val | Met | Ala | Lys | Ile | Gln | Asn | Gln | Gln | Leu | Thr | Leu | Ser | Ile | Val | |
| | | 915 | | | | | 920 | | | | | 925 | | | | |
| AAT | CCT | GAT | TTA | AAT | TTA | TAT | CAA | GGT | AGA | GAA | AAA | GAT | CAA | TTT | GAT | 6069 |
| Asn | Pro | Asp | Leu | Asn | Leu | Tyr | Gln | Gly | Arg | Glu | Lys | Asp | Gln | Phe | Asp | |
| | 930 | | | | | 935 | | | | | 940 | | | | | |
| GAT | AAA | GGT | AAT | CAA | ATC | GAA | GTT | AGT | GTT | TAT | TCT | CGT | CAT | TGG | CTT | 6117 |
| Asp | Lys | Gly | Asn | Gln | Ile | Glu | Val | Ser | Val | Tyr | Ser | Arg | His | Trp | Leu | |
| 945 | | | | | 950 | | | | | 955 | | | | | 960 | |
| ACA | GCA | GAA | TCG | CAA | TCA | ACA | AAT | AGT | ACT | ATT | ACC | GTA | AAA | GGA | ATA | 6165 |
| Thr | Ala | Glu | Ser | Gln | Ser | Thr | Asn | Ser | Thr | Ile | Thr | Val | Lys | Gly | Ile | |
| | | | | 965 | | | | | 970 | | | | | 975 | | |
| TGG | AAA | TTA | ACG | ACA | CCT | CAA | CCC | GGT | GTT | ATT | ATT | AAG | CAC | CAC | AAT | 6213 |
| Trp | Lys | Leu | Thr | Thr | Pro | Gln | Pro | Gly | Val | Ile | Ile | Lys | His | His | Asn | |
| | | | 980 | | | | | 985 | | | | | 990 | | | |
| AAC | AAC | ACT | CTT | ATT | ACG | ACA | ACA | ACC | ATA | CAG | GCA | ACA | CCT | ACT | GTT | 6261 |
| Asn | Asn | Thr | Leu | Ile | Thr | Thr | Thr | Thr | Ile | Gln | Ala | Thr | Pro | Thr | Val | |
| | | 995 | | | | | 1000 | | | | | 1005 | | | | |
| ATT | AAT | TTA | GTT | AAG | TAAATTTCGT | AACTTTTAAA | CTAAAGAGTC | TCGACATAAA | | | | | | | | 6316 |
| Ile | Asn | Leu | Val | Lys | | | | | | | | | | | | |
| | | 1010 | | | | | | | | | | | | | | |
| AATATCGAGA | CTCTTTTTAT | TAAAAAATTA | AAAACAAGTT | AACGAATGAA | TTAATTATTT | | | | | | | | | | | 6376 |

```
GAAAAATAAA AAATAAATCG ATAGCTTTAT TATTGATAAT AAATGTGTTG TGCTCAATGG    6436

TTATTTTGTT ATTCTCTGCG CGGATGCTTG GATCAATCTG GTTCAAGCAT ATCGCAAGCA    6496

CCAGAACGAA AAAAGCCCCG GGT                                            6519
```

( 2 ) INFORMATION FOR SEQ ID NO:8:

( i ) SEQUENCE CHARACTERISTICS:
        ( A ) LENGTH: 1013 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Leu Ile Lys Asn Pro Leu Ala His Ala Val Thr Leu Ser Leu Cys
  1               5                  10                  15

Leu Ser Leu Pro Ala Gln Ala Leu Pro Thr Leu Ser His Glu Ala Phe
             20                  25                  30

Gly Asp Ile Tyr Leu Phe Glu Gly Glu Leu Pro Asn Thr Leu Thr Thr
         35                  40                  45

Ser Asn Asn Asn Gln Leu Ser Leu Ser Lys Gln His Ala Lys Asp Gly
 50                  55                  60

Glu Gln Ser Leu Lys Trp Gln Tyr Gln Pro Gln Ala Thr Leu Thr Leu
 65                  70                  75                  80

Asn Asn Ile Val Asn Tyr Gln Asp Asp Lys Asn Thr Ala Thr Pro Leu
                 85                  90                  95

Thr Phe Met Met Trp Ile Tyr Asn Glu Lys Pro Gln Ser Ser Pro Leu
            100                 105                 110

Thr Leu Ala Phe Lys Gln Asn Asn Lys Ile Ala Leu Ser Phe Asn Ala
            115                 120                 125

Glu Leu Asn Phe Thr Gly Trp Arg Gly Ile Ala Val Pro Phe Arg Asp
130                 135                 140

Met Gln Gly Ser Ala Thr Gly Gln Leu Asp Gln Leu Val Ile Thr Ala
145                 150                 155                 160

Pro Asn Gln Ala Gly Thr Leu Phe Phe Asp Gln Ile Ile Met Ser Val
                165                 170                 175

Pro Leu Asp Asn Arg Trp Ala Val Pro Asp Tyr Gln Thr Pro Tyr Val
            180                 185                 190

Asn Asn Ala Val Asn Thr Met Val Ser Lys Asn Trp Ser Ala Leu Leu
            195                 200                 205

Met Tyr Asp Gln Met Phe Gln Ala His Tyr Pro Thr Leu Asn Phe Asp
210                 215                 220

Thr Glu Phe Arg Asp Asp Gln Thr Glu Met Ala Ser Ile Tyr Gln Arg
225                 230                 235                 240

Phe Glu Tyr Tyr Gln Gly Ile Arg Ser Asp Lys Lys Ile Thr Pro Asp
                245                 250                 255

Met Leu Asp Lys His Leu Ala Leu Trp Glu Lys Leu Val Leu Thr Gln
            260                 265                 270

His Ala Asp Gly Ser Ile Thr Gly Lys Ala Leu Asp His Pro Asn Arg
            275                 280                 285

Gln His Phe Met Lys Val Glu Gly Val Phe Ser Glu Gly Thr Gln Lys
            290                 295                 300

Ala Leu Leu Asp Ala Asn Met Leu Arg Asp Val Gly Lys Thr Leu Leu
305                 310                 315                 320

Gln Thr Ala Ile Tyr Leu Arg Ser Asp Ser Leu Ser Ala Thr Asp Arg
```

|     |     |     |     | 325 |     |     |     |     | 330 |     |     |     |     | 335 |     |
| --- | --- | --- | --- | --- | --- | --- | --- | --- | --- | --- | --- | --- | --- | --- | --- |
| Lys | Lys | Leu | Glu<br>340 | Glu | Arg | Tyr | Leu | Leu<br>345 | Gly | Thr | Arg | Tyr<br>350 | Val | Leu | Glu |
| Gln | Gly | Phe<br>355 | Thr | Arg | Gly | Ser | Gly<br>360 | Tyr | Gln | Ile | Ile | Thr<br>365 | His | Val | Gly |
| Tyr | Gln<br>370 | Thr | Arg | Glu | Leu | Phe<br>375 | Asp | Ala | Trp | Phe | Ile<br>380 | Gly | Arg | His | Val |
| Leu<br>385 | Ala | Lys | Asn | Asn | Leu<br>390 | Ala | Pro | Thr | Gln | Gln<br>395 | Ala | Met | Met | Trp | 400 |
| Tyr | Asn | Ala | Thr | Gly<br>405 | Arg | Ile | Phe | Glu | Lys<br>410 | Asn | Asn | Glu | Ile | Val<br>415 | Asp |
| Ala | Asn | Val | Asp<br>420 | Ile | Leu | Asn | Thr | Gln<br>425 | Leu | Gln | Trp | Met | Ile<br>430 | Lys | Ser |
| Leu | Leu | Met<br>435 | Leu | Pro | Asp | Tyr | Gln<br>440 | Gln | Arg | Gln | Gln | Ala<br>445 | Leu | Ala | Gln |
| Leu | Gln<br>450 | Ser | Trp | Leu | Asn | Lys<br>455 | Thr | Ile | Leu | Ser | Ser<br>460 | Lys | Gly | Val | Ala |
| Gly<br>465 | Gly | Phe | Lys | Ser | Asp<br>470 | Gly | Ser | Ile | Phe | His<br>475 | His | Ser | Gln | His | Tyr<br>480 |
| Pro | Ala | Tyr | Ala | Lys<br>485 | Asp | Ala | Phe | Gly | Gly<br>490 | Leu | Ala | Pro | Ser | Val<br>495 | Tyr |
| Ala | Leu | Ser | Asp<br>500 | Ser | Pro | Phe | Arg | Leu<br>505 | Ser | Thr | Ser | Ala | His<br>510 | Glu | Arg |
| Leu | Lys | Asp<br>515 | Val | Leu | Leu | Lys | Met<br>520 | Arg | Ile | Tyr | Thr | Lys<br>525 | Glu | Thr | Gln |
| Ile | Pro<br>530 | Val | Val | Leu | Ser | Gly<br>535 | Arg | His | Pro | Thr | Gly<br>540 | Leu | His | Lys | Ile |
| Gly<br>545 | Ile | Ala | Pro | Phe | Lys<br>550 | Trp | Met | Ala | Leu | Ala<br>555 | Gly | Thr | Pro | Asp | Gly<br>560 |
| Lys | Gln | Lys | Leu | Asp<br>565 | Thr | Thr | Leu | Ser | Ala<br>570 | Ala | Tyr | Ala | Lys | Leu<br>575 | Asp |
| Asn | Lys | Thr | His<br>580 | Phe | Glu | Gly | Ile | Asn<br>585 | Ala | Glu | Ser | Glu | Pro<br>590 | Val | Gly |
| Ala | Trp | Ala<br>595 | Met | Asn | Tyr | Ala | Ser<br>600 | Met | Ala | Ile | Gln | Arg<br>605 | Arg | Ala | Ser |
| Thr | Gln<br>610 | Ser | Pro | Gln | Gln | Ser<br>615 | Trp | Leu | Ala | Ile | Ala<br>620 | Arg | Gly | Phe | Ser |
| Arg<br>625 | Tyr | Leu | Val | Gly | Asn<br>630 | Glu | Ser | Tyr | Glu | Asn<br>635 | Asn | Arg | Tyr | Gly | 640 |
| Arg | Tyr | Leu | Gln | Tyr<br>645 | Gly | Gln | Leu | Glu | Ile<br>650 | Ile | Pro | Ala | Asp | Leu<br>655 | Thr |
| Gln | Ser | Gly | Phe<br>660 | Ser | His | Ala | Gly | Trp<br>665 | Asp | Trp | Asn | Arg | Tyr<br>670 | Pro | Gly |
| Thr | Thr | Thr<br>675 | Ile | His | Leu | Pro | Tyr<br>680 | Asn | Glu | Leu | Glu | Ala<br>685 | Lys | Leu | Asn |
| Gln | Leu<br>690 | Pro | Ala | Ala | Gly | Ile<br>695 | Glu | Glu | Met | Leu | Leu<br>700 | Ser | Thr | Glu | Ser |
| Tyr<br>705 | Ser | Gly | Ala | Asn | Thr<br>710 | Leu | Asn | Asn | Asn | Ser<br>715 | Met | Phe | Ala | Met | Lys<br>720 |
| Leu | His | Gly | His | Ser<br>725 | Lys | Tyr | Gln | Gln | Gln<br>730 | Ser | Leu | Arg | Ala | Asn<br>735 | Lys |
| Ser | Tyr | Phe | Leu<br>740 | Phe | Asp | Asn | Arg | Val<br>745 | Ile | Ala | Leu | Gly | Ser<br>750 | Gly | Ile |

-continued

```
Glu  Asn  Asp  Asp  Lys  Gln  His  Thr  Thr  Glu  Thr  Thr  Leu  Phe  Gln  Phe
          755                      760                     765
Ala  Val  Pro  Lys  Leu  Gln  Ser  Val  Ile  Ile  Asn  Gly  Lys  Lys  Val  Asn
     770                      775                     780
Gln  Leu  Asp  Thr  Gln  Leu  Thr  Leu  Asn  Asn  Ala  Asp  Thr  Leu  Ile  Asp
785                      790                     795                          800
Pro  Ala  Gly  Asn  Leu  Tyr  Lys  Leu  Thr  Lys  Gly  Gln  Thr  Val  Lys  Phe
                    805                     810                     815
Ser  Tyr  Gln  Lys  Gln  His  Ser  Leu  Asp  Asp  Arg  Asn  Ser  Lys  Pro  Thr
               820                     825                     830
Glu  Gln  Leu  Phe  Ala  Thr  Ala  Val  Ile  Ser  His  Gly  Lys  Ala  Pro  Ser
          835                      840                     845
Asn  Glu  Asn  Tyr  Glu  Tyr  Ala  Ile  Ala  Ile  Glu  Ala  Gln  Asn  Asn  Lys
     850                      855                     860
Ala  Pro  Glu  Tyr  Thr  Val  Leu  Gln  His  Asn  Asp  Gln  Leu  His  Ala  Val
865                           870                     875                     880
Lys  Asp  Lys  Ile  Thr  Gln  Glu  Glu  Gly  Tyr  Ala  Phe  Phe  Glu  Ala  Thr
                    885                     890                          895
Lys  Leu  Lys  Ser  Ala  Asp  Ala  Thr  Leu  Leu  Ser  Ser  Asp  Ala  Pro  Val
               900                     905                     910
Met  Val  Met  Ala  Lys  Ile  Gln  Asn  Gln  Gln  Leu  Thr  Leu  Ser  Ile  Val
          915                     920                      925
Asn  Pro  Asp  Leu  Asn  Leu  Tyr  Gln  Gly  Arg  Glu  Lys  Asp  Gln  Phe  Asp
     930                      935                     940
Asp  Lys  Gly  Asn  Gln  Ile  Glu  Val  Ser  Val  Tyr  Ser  Arg  His  Trp  Leu
945                      950                     955                          960
Thr  Ala  Glu  Ser  Gln  Ser  Thr  Asn  Ser  Thr  Ile  Thr  Val  Lys  Gly  Ile
               965                     970                     975
Trp  Lys  Leu  Thr  Thr  Pro  Gln  Pro  Gly  Val  Ile  Ile  Lys  His  His  Asn
          980                     985                      990
Asn  Asn  Thr  Leu  Ile  Thr  Thr  Thr  Ile  Gln  Ala  Thr  Pro  Thr  Val
          995                     1000                    1005
Ile  Asn  Leu  Val  Lys
     1010
```